US011903661B2

(12) United States Patent
DeFonzo et al.

(10) Patent No.: US 11,903,661 B2
(45) Date of Patent: Feb. 20, 2024

(54) SYSTEMS AND METHODS FOR CONCOMITANT MEDICAL PROCEDURES

(71) Applicant: Auris Health, Inc., Redwood City, CA (US)

(72) Inventors: Joshua F. DeFonzo, San Carlos, CA (US); Alexander Tarek Hassan, San Francisco, CA (US); Frederic H. Moll, San Francisco, CA (US); David Stephen Mintz, Los Altos Hills, CA (US); David M. Schummers, Oakland, CA (US); Paxton H. Maeder-York, Cambridge, MA (US); Andrew F. O'Rourke, Los Angeles, CA (US)

(73) Assignee: Auris Health, Inc., Redwood City, CA (US)

(*) Notice: Subject to any disclaimer, the term of this patent is extended or adjusted under 35 U.S.C. 154(b) by 0 days.

(21) Appl. No.: 17/545,993

(22) Filed: Dec. 8, 2021

(65) Prior Publication Data
US 2022/0096178 A1 Mar. 31, 2022

Related U.S. Application Data

(63) Continuation of application No. 16/559,310, filed on Sep. 3, 2019, now Pat. No. 11,197,728.
(Continued)

(51) Int. Cl.
*A61B 34/30* (2016.01)
*A61B 34/37* (2016.01)
(Continued)

(52) U.S. Cl.
CPC ............ *A61B 34/30* (2016.02); *A61B 1/0005* (2013.01); *A61B 1/00149* (2013.01);
(Continued)

(58) Field of Classification Search
CPC ...... A61G 13/101; A61G 13/04; A61G 13/08; A61G 13/1235; A61G 13/10;
(Continued)

(56) References Cited

U.S. PATENT DOCUMENTS

| 5,199,417 A | 4/1993 | Muller et al. |
| 5,876,325 A * | 3/1999 | Mizuno ................. A61B 34/37 600/117 |

(Continued)

FOREIGN PATENT DOCUMENTS

| EP | 0 347 098 | 2/1996 |
| JP | 2005-511334 A | 4/2005 |

(Continued)

OTHER PUBLICATIONS

International Search Report and Written Opinion dated Nov. 12, 2019 in application No. PCT/US2019/049299.
(Continued)

*Primary Examiner* — Stephen Holwerda
(74) *Attorney, Agent, or Firm* — Conley Rose, P.C.

(57) ABSTRACT

Systems and methods for performing concomitant medical procedures are disclosed. In one aspect, the method involves controlling a first robotic arm to insert a first medical instrument through a first opening of a patient and controlling a second robotic arm to insert a second medical instrument through a second opening of the patient. The first robotic arm and the second robotic arm are part of a first platform and the first opening and the second opening are positioned at two different anatomical regions of the patient.

19 Claims, 35 Drawing Sheets

Related U.S. Application Data

(60) Provisional application No. 62/732,478, filed on Sep. 17, 2018.

(51) Int. Cl.

| | | |
|---|---|---|
| *A61B 50/13* | (2016.01) | |
| *A61B 1/267* | (2006.01) | |
| *A61B 1/273* | (2006.01) | |
| *A61B 10/04* | (2006.01) | |
| *A61B 1/307* | (2006.01) | |
| *A61B 34/20* | (2016.01) | |
| *A61B 1/00* | (2006.01) | |
| *A61G 13/10* | (2006.01) | |
| *B25J 9/00* | (2006.01) | |
| *B25J 15/00* | (2006.01) | |
| *B25J 13/06* | (2006.01) | |
| *A61B 34/00* | (2016.01) | |
| *A61B 6/03* | (2006.01) | |

(52) U.S. Cl.
CPC ............ *A61B 1/2676* (2013.01); *A61B 1/273* (2013.01); *A61B 1/307* (2013.01); *A61B 10/04* (2013.01); *A61B 34/20* (2016.02); *A61B 34/25* (2016.02); *A61B 34/37* (2016.02); *A61B 50/13* (2016.02); *A61G 13/10* (2013.01); *B25J 9/0087* (2013.01); *B25J 13/065* (2013.01); *B25J 15/0019* (2013.01); *A61B 6/032* (2013.01); *A61B 2010/045* (2013.01); *A61B 2034/2051* (2016.02); *A61B 2034/301* (2016.02); *A61B 2034/303* (2016.02); *A61B 2034/304* (2016.02)

(58) Field of Classification Search
CPC ... A61G 13/104; B25J 15/0019; B25J 9/0087; B25J 13/065; A61B 34/25; A61B 1/0005; A61B 1/273; A61B 50/13; A61B 34/37; A61B 34/20; A61B 1/00149; A61B 1/2676; A61B 10/04; A61B 1/307; A61B 34/30; A61B 2034/2061; A61B 2034/105; A61B 2034/301; A61B 2034/2065; A61B 2090/376; A61B 2017/00809; A61B 2090/306; A61B 2034/2051; A61B 2010/045; A61B 2034/2059; A61B 2090/3614; A61B 6/032; A61B 2034/304; A61B 2090/371; A61B 2034/303

See application file for complete search history.

(56) References Cited

U.S. PATENT DOCUMENTS

| | | | |
|---|---|---|---|
| 6,044,846 A * | 4/2000 | Edwards | A61N 1/056 606/41 |
| 6,424,885 B1 | 7/2002 | Niemeyer et al. | |
| 6,441,577 B2 | 8/2002 | Blumenkranz et al. | |
| 6,503,195 B1 | 1/2003 | Keller et al. | |
| 6,659,939 B2 | 12/2003 | Moll et al. | |
| 6,671,581 B2 | 12/2003 | Niemeyer et al. | |
| 6,728,599 B2 | 4/2004 | Wang et al. | |
| 6,785,593 B2 | 8/2004 | Wang et al. | |
| 6,788,018 B1 | 9/2004 | Blumenkranz | |
| 6,799,088 B2 | 9/2004 | Wang et al. | |
| 6,836,703 B2 | 12/2004 | Wang et al. | |
| 6,837,883 B2 | 1/2005 | Moll et al. | |
| 6,858,003 B2 | 2/2005 | Evans et al. | |
| 6,892,112 B2 | 5/2005 | Wang et al. | |
| 7,155,315 B2 | 12/2006 | Niemeyer et al. | |
| 7,574,250 B2 | 8/2009 | Niemeyer | |
| 7,607,440 B2 | 10/2009 | Coste-Maniere et al. | |
| 7,865,266 B2 | 1/2011 | Moll et al. | |
| 7,907,166 B2 | 3/2011 | Lamprecht et al. | |
| 7,914,521 B2 | 3/2011 | Wang et al. | |
| 8,021,326 B2 | 9/2011 | Moll et al. | |
| 8,170,716 B2 | 5/2012 | Coste-Maniere et al. | |
| 8,398,541 B2 | 3/2013 | DiMaio et al. | |
| 8,418,073 B2 | 4/2013 | Mohr et al. | |
| 8,489,235 B2 | 7/2013 | Moll et al. | |
| 8,527,094 B2 | 9/2013 | Kumar et al. | |
| 8,545,515 B2 | 10/2013 | Prisco et al. | |
| 8,571,710 B2 | 10/2013 | Coste-Maniere et al. | |
| 8,652,030 B2 | 2/2014 | Matsuura et al. | |
| 8,682,416 B2 | 3/2014 | Lin et al. | |
| 8,828,023 B2 | 9/2014 | Neff et al. | |
| 8,834,489 B2 | 9/2014 | Cooper et al. | |
| 8,888,789 B2 | 11/2014 | Prisco et al. | |
| 8,918,207 B2 | 12/2014 | Prisco | |
| 9,173,548 B2 | 11/2015 | Omori | |
| 9,232,984 B2 | 1/2016 | Guthart et al. | |
| 9,254,178 B2 | 2/2016 | Prisco et al. | |
| 9,266,239 B2 | 2/2016 | Miller | |
| 9,271,798 B2 | 3/2016 | Kumar et al. | |
| 9,504,604 B2 | 11/2016 | Alvarez | |
| 9,532,838 B2 | 1/2017 | Coste-Maniere et al. | |
| 9,554,827 B2 | 1/2017 | Omori | |
| 9,561,083 B2 | 2/2017 | Yu et al. | |
| 9,622,827 B2 | 4/2017 | Yu et al. | |
| 9,636,184 B2 | 5/2017 | Lee et al. | |
| 9,636,186 B2 | 5/2017 | Kumar et al. | |
| 9,668,768 B2 | 6/2017 | Piron et al. | |
| 9,713,509 B2 | 7/2017 | Schuh et al. | |
| 9,717,563 B2 | 8/2017 | Tognaccini | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,782,229 B2 | 10/2017 | Crawford | |
| 9,788,910 B2 | 10/2017 | Schuh | |
| 9,814,527 B2 | 11/2017 | Rogers et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,931,173 B2 | 4/2018 | Prisco et al. | |
| 9,943,964 B2 | 4/2018 | Hares | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,010,375 B2 | 7/2018 | Jeong et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,500,001 B2 | 12/2019 | Yu et al. | |
| 10,517,692 B2 | 12/2019 | Eyre et al. | |

(56) References Cited

U.S. PATENT DOCUMENTS

| | | | |
|---|---|---|---|
| 10,524,866 B2 | 1/2020 | Srinivasan | |
| 10,539,478 B2 | 1/2020 | Un | |
| 10,543,048 B2 | 1/2020 | Noonan et al. | |
| 10,639,109 B2 | 5/2020 | Bovay et al. | |
| 10,639,114 B2 | 5/2020 | Schuh | |
| 10,646,291 B2 | 5/2020 | Turner | |
| 10,765,487 B2 | 9/2020 | Ho | |
| 11,197,728 B2* | 12/2021 | DeFonzo | B25J 9/0087 |
| 2002/0058929 A1 | 5/2002 | Green | |
| 2002/0082612 A1* | 6/2002 | Moll | G16H 40/63 606/130 |
| 2003/0013949 A1 | 1/2003 | Moll et al. | |
| 2003/0065311 A1 | 4/2003 | Wang et al. | |
| 2003/0078474 A1 | 4/2003 | Wang et al. | |
| 2003/0083648 A1 | 5/2003 | Wang et al. | |
| 2003/0181809 A1 | 9/2003 | Hall et al. | |
| 2004/0006339 A1* | 1/2004 | Underwood | A61B 18/149 606/228 |
| 2004/0176751 A1 | 9/2004 | Weitzner et al. | |
| 2004/0236352 A1 | 11/2004 | Wang et al. | |
| 2005/0107808 A1 | 5/2005 | Evans et al. | |
| 2005/0228365 A1 | 10/2005 | Wang et al. | |
| 2006/0058617 A1 | 3/2006 | Sano et al. | |
| 2006/0178556 A1 | 8/2006 | Hasser et al. | |
| 2007/0021738 A1 | 1/2007 | Hasser et al. | |
| 2007/0038080 A1 | 2/2007 | Salisbury et al. | |
| 2008/0033240 A1 | 2/2008 | Hoffman et al. | |
| 2008/0147089 A1 | 6/2008 | Loh | |
| 2009/0005768 A1 | 1/2009 | Sharareh | |
| 2009/0048611 A1 | 2/2009 | Funda | |
| 2009/0171374 A1 | 7/2009 | Omori | |
| 2009/0248041 A1 | 10/2009 | Williams et al. | |
| 2009/0326318 A1 | 12/2009 | Tognaccini | |
| 2010/0100045 A1 | 4/2010 | Pravongviengkham et al. | |
| 2010/0234857 A1 | 9/2010 | Itkowitz | |
| 2010/0262162 A1 | 10/2010 | Omori | |
| 2010/0286712 A1 | 11/2010 | Won | |
| 2011/0071541 A1 | 3/2011 | Prisco et al. | |
| 2011/0276058 A1 | 11/2011 | Choi et al. | |
| 2011/0277775 A1 | 11/2011 | Holop et al. | |
| 2012/0071894 A1 | 3/2012 | Tanner et al. | |
| 2012/0283747 A1 | 11/2012 | Popovic | |
| 2012/0302869 A1 | 11/2012 | Koyrakh | |
| 2013/0217967 A1 | 8/2013 | Mohr et al. | |
| 2014/0051049 A1 | 2/2014 | Jarc | |
| 2014/0142591 A1 | 5/2014 | Alvarez et al. | |
| 2014/0163359 A1 | 6/2014 | Sholev et al. | |
| 2014/0243801 A1 | 8/2014 | Fanelli et al. | |
| 2014/0357984 A1 | 12/2014 | Wallace et al. | |
| 2014/0364870 A1 | 12/2014 | Alvarez et al. | |
| 2015/0025549 A1 | 1/2015 | Kilroy et al. | |
| 2015/0045675 A1 | 2/2015 | Chernomorsky | |
| 2015/0088161 A1 | 3/2015 | Hata | |
| 2015/0119638 A1 | 4/2015 | Yu | |
| 2015/0223832 A1 | 8/2015 | Swaney | |
| 2015/0297299 A1 | 10/2015 | Yeung | |
| 2015/0305650 A1 | 10/2015 | Hunter | |
| 2016/0001038 A1 | 1/2016 | Romo et al. | |
| 2016/0184032 A1 | 6/2016 | Romo et al. | |
| 2016/0206179 A1 | 7/2016 | Luo | |
| 2016/0235496 A1 | 8/2016 | Hoffman et al. | |
| 2016/0270865 A1 | 9/2016 | Landey et al. | |
| 2016/0287279 A1 | 10/2016 | Bovay et al. | |
| 2016/0331613 A1* | 11/2016 | Lee | A61G 13/02 |
| 2017/0007337 A1 | 1/2017 | Dan | |
| 2017/0071456 A1 | 3/2017 | Ratnakar | |
| 2017/0095299 A1 | 4/2017 | Hendrick | |
| 2017/0119481 A1 | 5/2017 | Romo et al. | |
| 2017/0135710 A1 | 5/2017 | Hasegawa et al. | |
| 2017/0135833 A1 | 5/2017 | Syed | |
| 2017/0143442 A1 | 5/2017 | Tesar | |
| 2017/0165011 A1 | 6/2017 | Bovay et al. | |
| 2017/0172673 A1 | 6/2017 | Yu et al. | |
| 2017/0180704 A1 | 6/2017 | Panescu et al. | |
| 2017/0181808 A1 | 6/2017 | Panescu et al. | |
| 2017/0189118 A1 | 7/2017 | Chopra | |
| 2017/0189131 A1 | 7/2017 | Weir | |
| 2017/0202627 A1 | 7/2017 | Sramek et al. | |
| 2017/0209073 A1 | 7/2017 | Sramek et al. | |
| 2017/0239009 A1 | 8/2017 | Cooper et al. | |
| 2017/0290631 A1 | 10/2017 | Iee et al. | |
| 2017/0333141 A1 | 11/2017 | Itkowitz et al. | |
| 2017/0340396 A1 | 11/2017 | Romo et al. | |
| 2017/0367782 A1 | 12/2017 | Schuh et al. | |
| 2018/0020932 A1 | 1/2018 | Chen et al. | |
| 2018/0025666 A1 | 1/2018 | Ho et al. | |
| 2018/0036084 A1 | 2/2018 | Krimsky | |
| 2018/0078440 A1 | 3/2018 | Koenig | |
| 2018/0098817 A1 | 4/2018 | Nichogi et al. | |
| 2018/0186005 A1 | 7/2018 | Hares | |
| 2018/0214011 A1 | 8/2018 | Graetzel et al. | |
| 2018/0221038 A1 | 8/2018 | Noonan et al. | |
| 2018/0221039 A1 | 8/2018 | Shah | |
| 2018/0250083 A1 | 9/2018 | Schuh et al. | |
| 2018/0271616 A1 | 9/2018 | Schuh et al. | |
| 2018/0279852 A1 | 10/2018 | Rafii-Tari et al. | |
| 2018/0280660 A1 | 10/2018 | Landey et al. | |
| 2018/0289431 A1 | 10/2018 | Draper et al. | |
| 2018/0325499 A1 | 11/2018 | Landey et al. | |
| 2018/0333044 A1 | 11/2018 | Jenkins | |
| 2018/0338799 A1 | 11/2018 | Hladio et al. | |
| 2018/0360435 A1 | 12/2018 | Romo | |
| 2018/0368920 A1 | 12/2018 | Ummalaneni | |
| 2019/0000559 A1 | 1/2019 | Berman et al. | |
| 2019/0000560 A1 | 1/2019 | Berman et al. | |
| 2019/0000576 A1 | 1/2019 | Mintz et al. | |
| 2019/0083183 A1 | 3/2019 | Moll et al. | |
| 2019/0110839 A1 | 4/2019 | Rafii-Tari et al. | |
| 2019/0110843 A1 | 4/2019 | Ummalaneni et al. | |
| 2019/0151148 A1 | 4/2019 | Alvarez et al. | |
| 2019/0167366 A1 | 6/2019 | Ummalaneni | |
| 2019/0175009 A1 | 6/2019 | Mintz | |
| 2019/0175062 A1 | 6/2019 | Rafii-Tari et al. | |
| 2019/0175799 A1 | 6/2019 | Hsu | |
| 2019/0183585 A1 | 6/2019 | Rafii-Tari et al. | |
| 2019/0183587 A1 | 6/2019 | Rafii-Tari et al. | |
| 2019/0216548 A1 | 7/2019 | Ummalaneni | |
| 2019/0216576 A1 | 7/2019 | Eyre | |
| 2019/0223974 A1 | 7/2019 | Romo | |
| 2019/0228525 A1 | 7/2019 | Mintz et al. | |
| 2019/0246882 A1 | 8/2019 | Graetzel et al. | |
| 2019/0262086 A1 | 8/2019 | Connolly et al. | |
| 2019/0269468 A1 | 9/2019 | Hsu et al. | |
| 2019/0274764 A1 | 9/2019 | Romo | |
| 2019/0290109 A1 | 9/2019 | Agrawal et al. | |
| 2019/0298160 A1 | 10/2019 | Ummalaneni et al. | |
| 2019/0298460 A1 | 10/2019 | Al-Jadda | |
| 2019/0298465 A1 | 10/2019 | Chin | |
| 2019/0328213 A1 | 10/2019 | Landey et al. | |
| 2019/0336238 A1 | 11/2019 | Yu | |
| 2019/0365201 A1 | 12/2019 | Noonan et al. | |
| 2019/0365209 A1 | 12/2019 | Ye et al. | |
| 2019/0365479 A1 | 12/2019 | Rafii-Tari | |
| 2019/0365486 A1 | 12/2019 | Srinivasan et al. | |
| 2019/0374297 A1 | 12/2019 | Wallace et al. | |
| 2019/0375383 A1 | 12/2019 | Alvarez | |
| 2019/0380787 A1 | 12/2019 | Ye | |
| 2019/0380797 A1 | 12/2019 | Yu | |
| 2020/0000530 A1 | 1/2020 | DeFonzo | |
| 2020/0000533 A1 | 1/2020 | Schuh | |
| 2020/0022767 A1 | 1/2020 | Hill | |
| 2020/0038123 A1 | 2/2020 | Graetzel | |
| 2020/0039086 A1 | 2/2020 | Meyer | |
| 2020/0046434 A1 | 2/2020 | Graetzel | |
| 2020/0054408 A1 | 2/2020 | Schuh et al. | |
| 2020/0060516 A1 | 2/2020 | Baez | |
| 2020/0093549 A1 | 3/2020 | Chin | |
| 2020/0093554 A1 | 3/2020 | Schuh | |
| 2020/0100845 A1 | 4/2020 | Julian | |
| 2020/0100853 A1 | 4/2020 | Ho | |
| 2020/0100855 A1 | 4/2020 | Leparmentier | |
| 2020/0101264 A1 | 4/2020 | Jiang | |
| 2020/0107894 A1 | 4/2020 | Wallace | |
| 2020/0121502 A1 | 4/2020 | Kintz | |

(56) References Cited

U.S. PATENT DOCUMENTS

| | | |
|---|---|---|
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0297437 A1 | 9/2020 | Schuh |
| 2020/0305983 A1 | 10/2020 | Yampolsky |
| 2020/0305989 A1 | 10/2020 | Schuh |
| 2020/0315717 A1 | 10/2020 | Bovay |
| 2020/0315723 A1 | 10/2020 | Moll |
| 2020/0323596 A1 | 10/2020 | Moll |
| 2020/0330167 A1 | 10/2020 | Romo |

FOREIGN PATENT DOCUMENTS

| | | |
|---|---|---|
| JP | 2009-178230 A | 8/2009 |
| JP | 2016-538006 A | 12/2016 |
| JP | 2017-502709 A | 1/2017 |
| JP | 2017-518147 A | 7/2017 |
| JP | 2018-500054 A | 1/2018 |
| WO | 2016/136676 A1 | 9/2016 |
| WO | WO 17/048194 | 3/2017 |

OTHER PUBLICATIONS

Darwiche, 2015, Operative technique and early experience for robotic assisted laparoscopic nephroureterectomy (RALNU) using da Vinci XI, SpringerPlus, 4:298.
Sasaki, 2017, Laparoscopic hemicolectomy for a patient with situs inversus totalis: a case report, Int. J. Surg. Case Rep. 41:93-96.
Notice of Reasons for Refusal; Japanese Patent Application No. 2021-507919; dated Jun. 27, 2023; 28 pages.

\* cited by examiner

SYSTEMS AND METHODS FOR CONCOMITANT MEDICAL PROCEDURES

CROSS-REFERENCE TO RELATED APPLICATIONS

This application is a continuation application of U.S. patent application Ser. No. 16/559,310, filed Sep. 3, 2019, which claims the benefit of U.S. Provisional Application No. 62/732,478, filed Sep. 17, 2018, both of which are incorporated by reference herein in their entireties.

TECHNICAL FIELD

The systems and methods disclosed herein are directed to systems and methods for performing medical procedures, and more particularly to concomitant procedures.

BACKGROUND

Various medical procedures may be performed using a robotic medical system to control the insertion and/or manipulation of one or more medical instruments. For certain medical conditions, two or more medical procedures may be performed to fully treat the medical condition. The robotic medical system may include one or more robotic arms or any other instrument positioning device(s). The robotic medical system may also include a controller used to control the positioning of the instrument(s) during each of the procedures via the manipulation of the robotic arm(s) and/or instrument positioning device(s).

SUMMARY

The systems, methods and devices of this disclosure each have several innovative aspects, no single one of which is solely responsible for the desirable attributes disclosed herein.

In one aspect, there is provided a method, comprising: controlling a first robotic arm to insert a first medical instrument through a first opening of a patient; and controlling a second robotic arm to insert a second medical instrument through a second opening of the patient, wherein the first robotic arm and the second robotic arm are part of a first platform, and wherein the first opening and the second opening are positioned at two different anatomical regions of the patient.

In another aspect, there is provided a method, comprising: using a user interface to operate a first instrument inserted through a first opening of a patient via a first robotic arm; and using the user interface to operate a second instrument inserted through a second opening of the patient via a second robotic arm, wherein the first opening and the second opening are positioned at two different anatomical regions of the patient.

In yet another aspect, there is provided a method, comprising: delivering a first scope through a first opening of a patient via a first robotic arm to obtain a first image; delivering a second scope through a second opening of the patient via a second robotic arm to obtain a second image; and toggling between the first image and the second image on a display.

In still yet another aspect, there is provided a method, comprising: controlling a first set of one or more robotic arms to insert a first medical instrument through a first opening of a patient; and controlling a second set of one or more robotic arms to insert a second medical instrument through a second opening of the patient, wherein the first set of robotic arms are coupled to a first arm support and the second set of robotic arms are coupled to a second arm support, and wherein the first opening and the second opening are positioned at two different anatomical regions of the patient.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
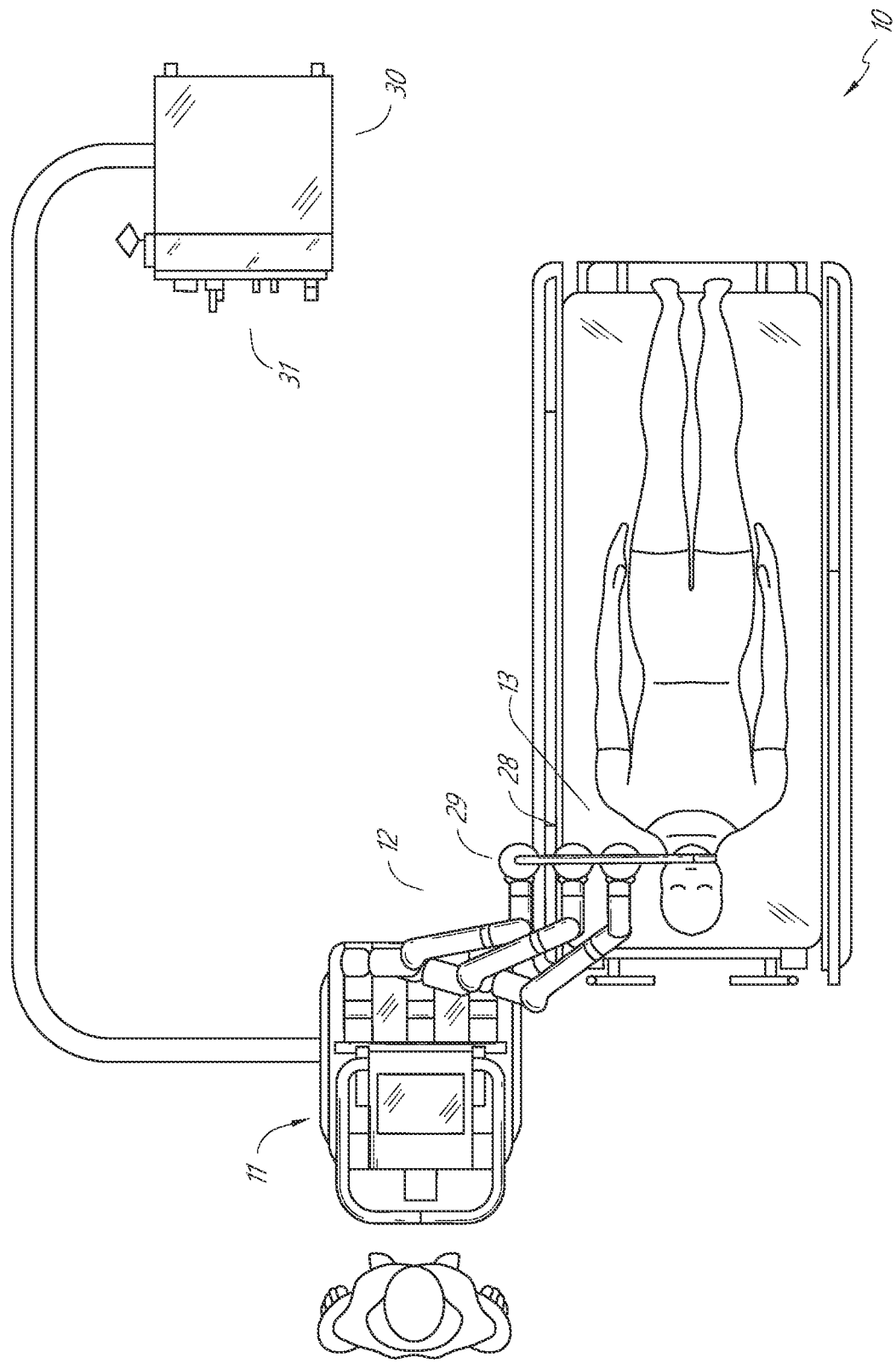
FIG. 1 illustrates an embodiment of a cart-based robotic system arranged for diagnostic and/or therapeutic bronchoscopy procedure(s).
Figure 2:
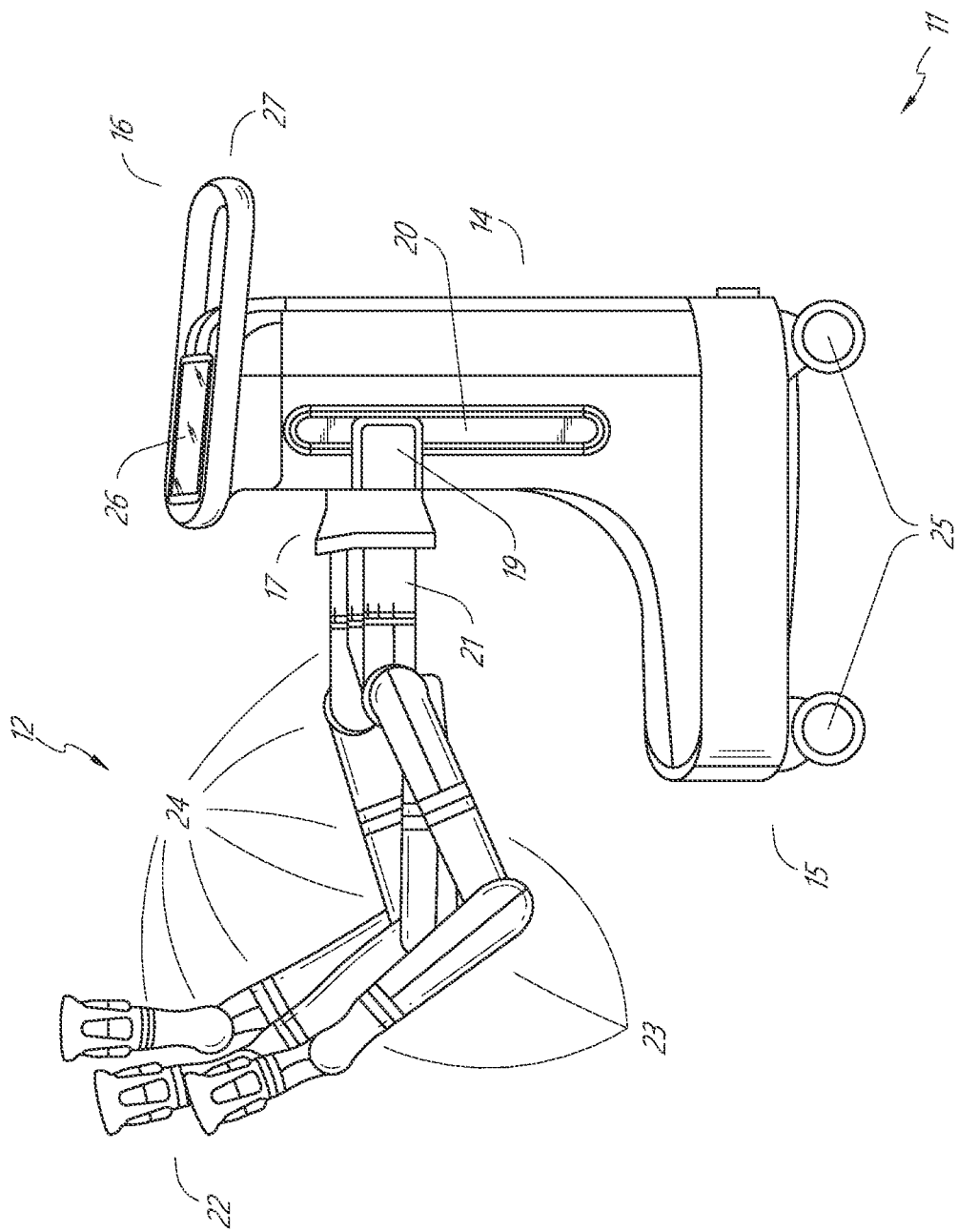
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastrointestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver (also referred to as an instrument drive mechanism (IDM)) from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or repositioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
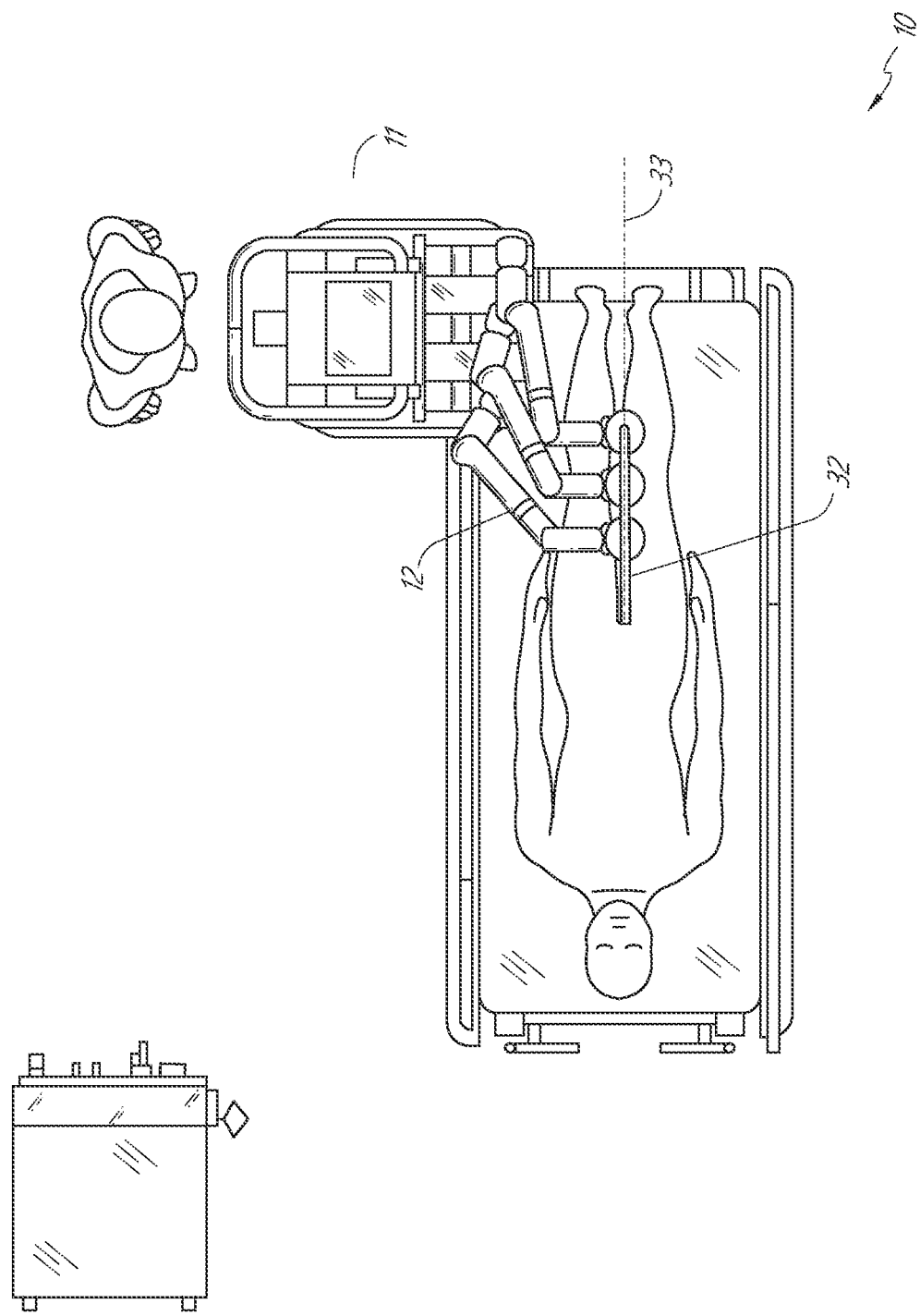
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may the insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
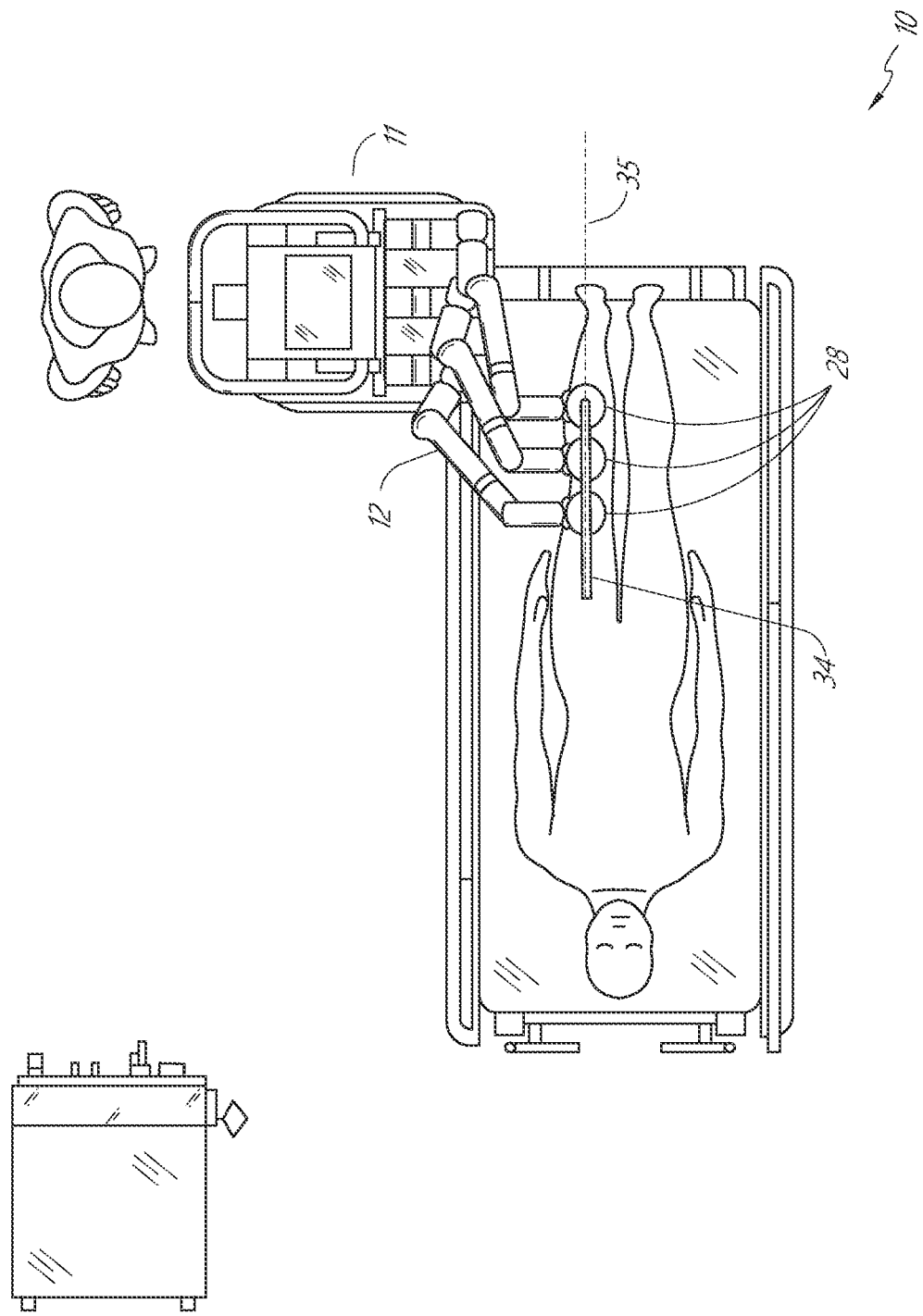
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
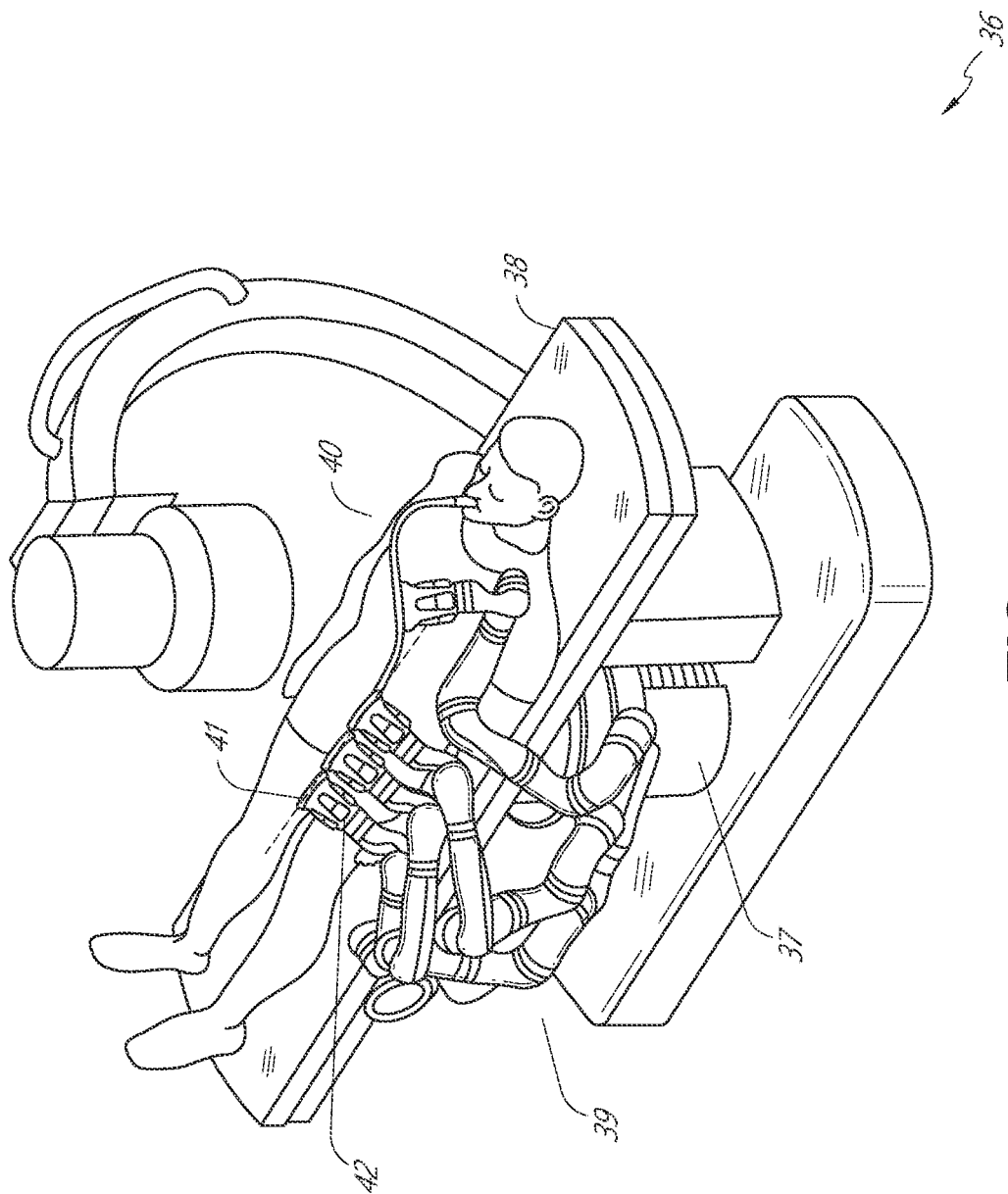
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
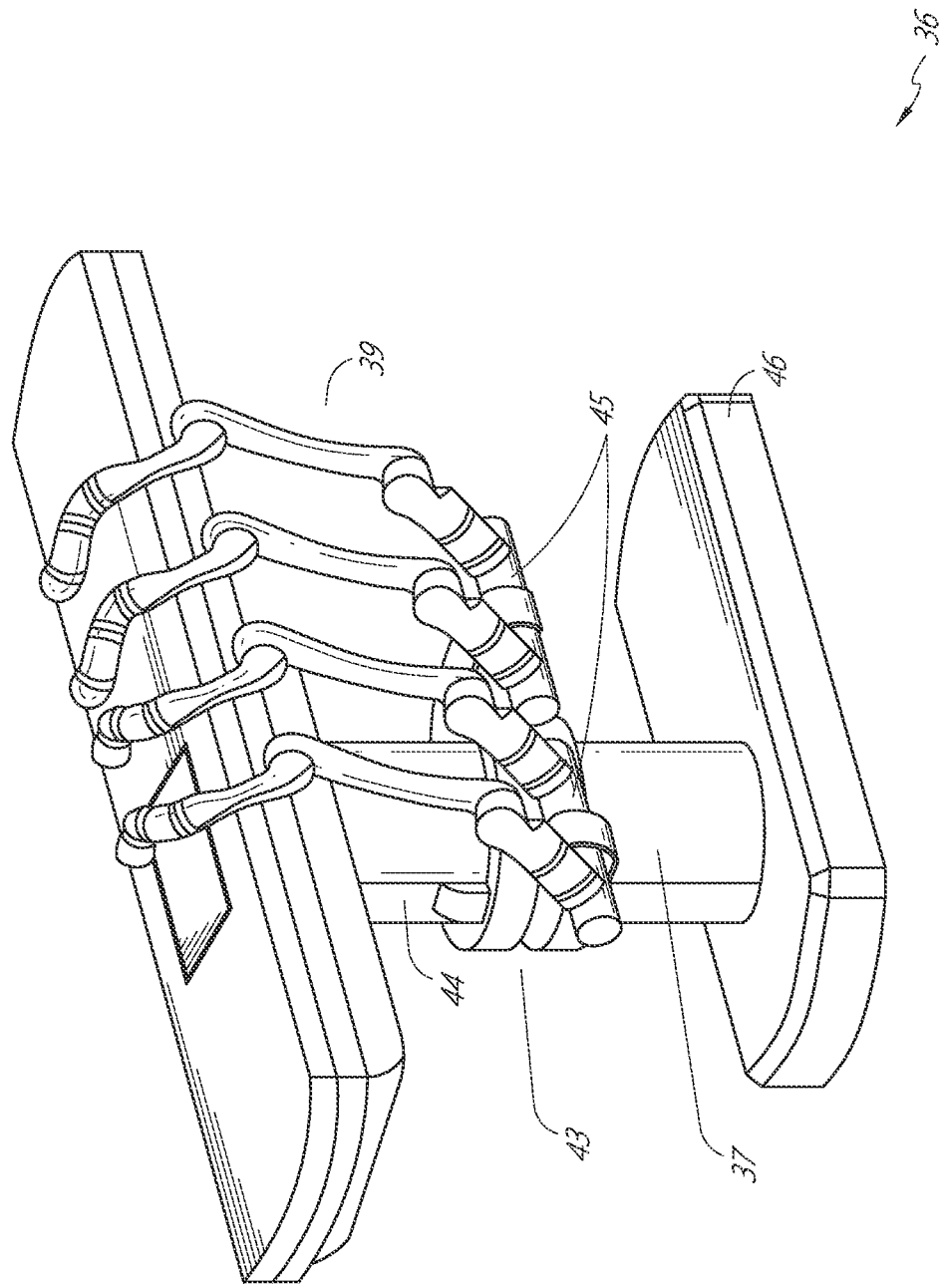
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
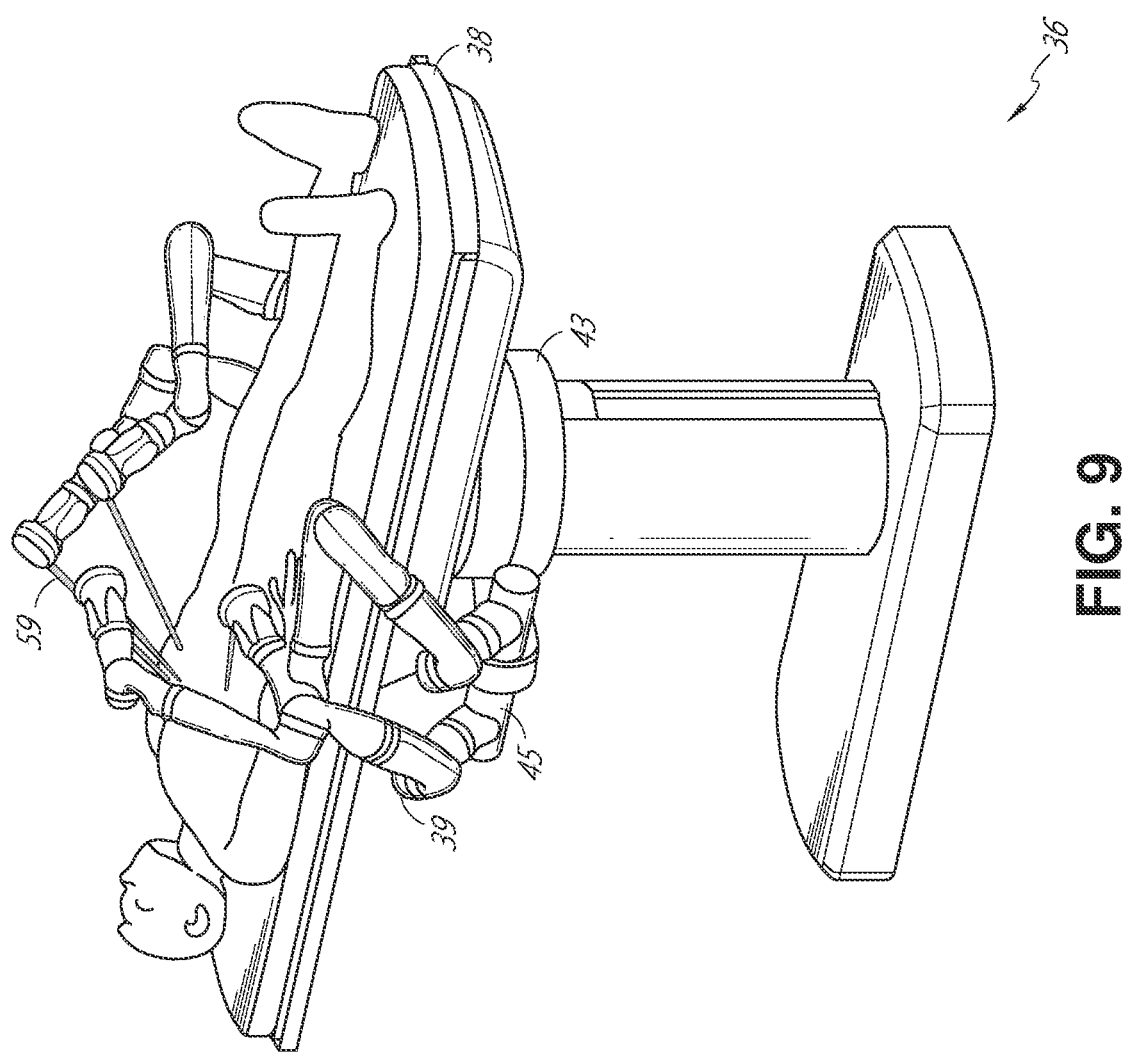
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
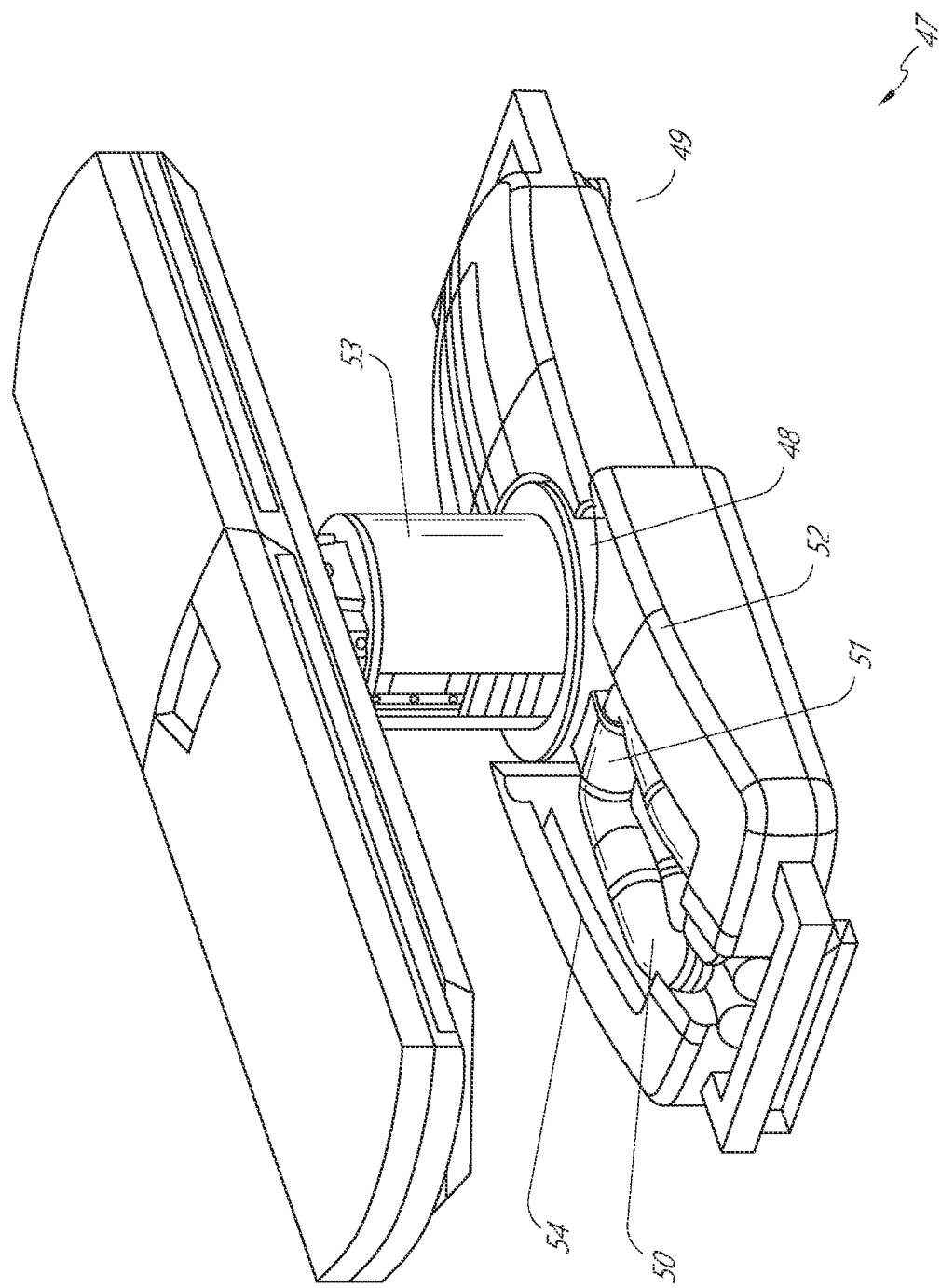
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
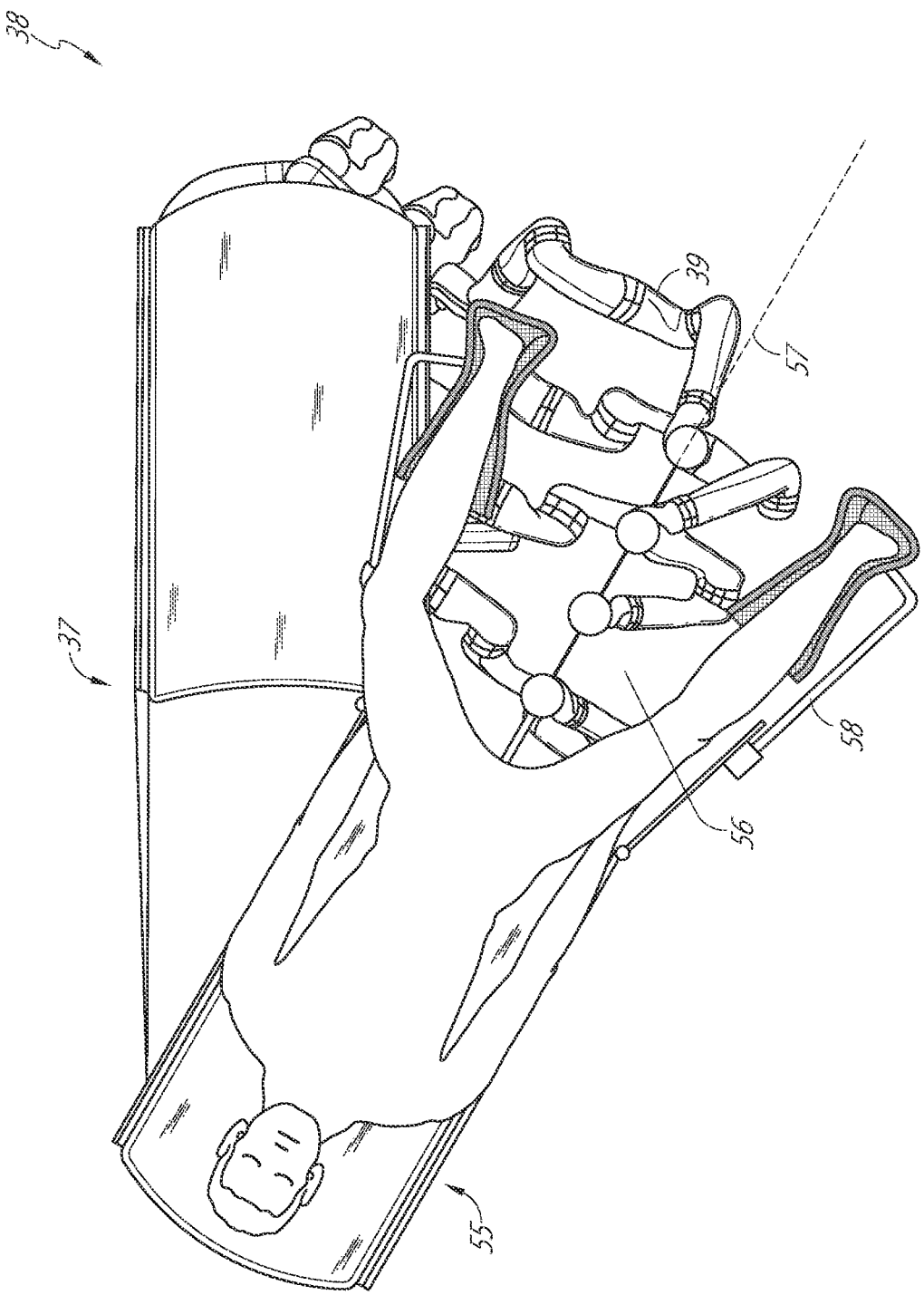
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
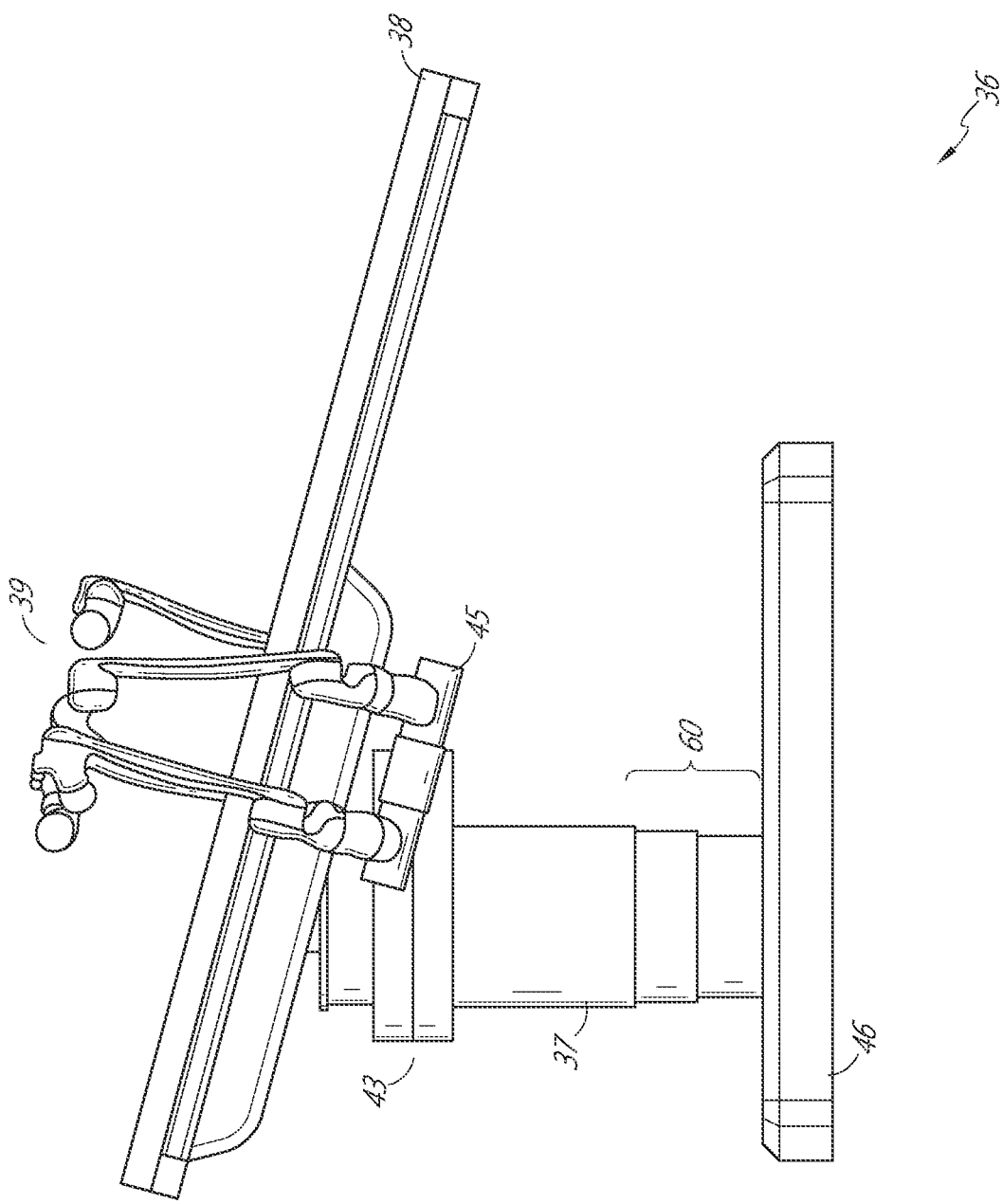
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
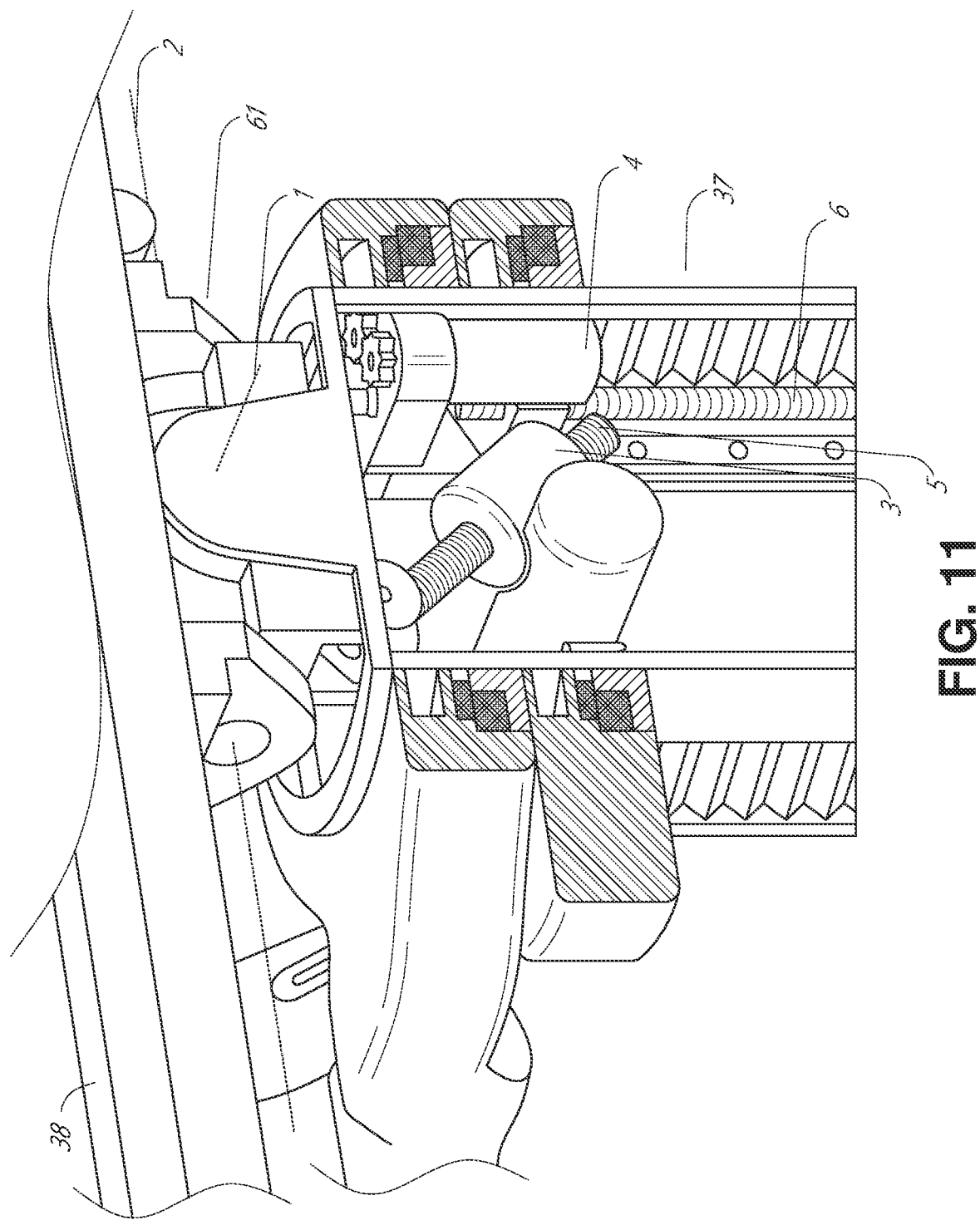
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
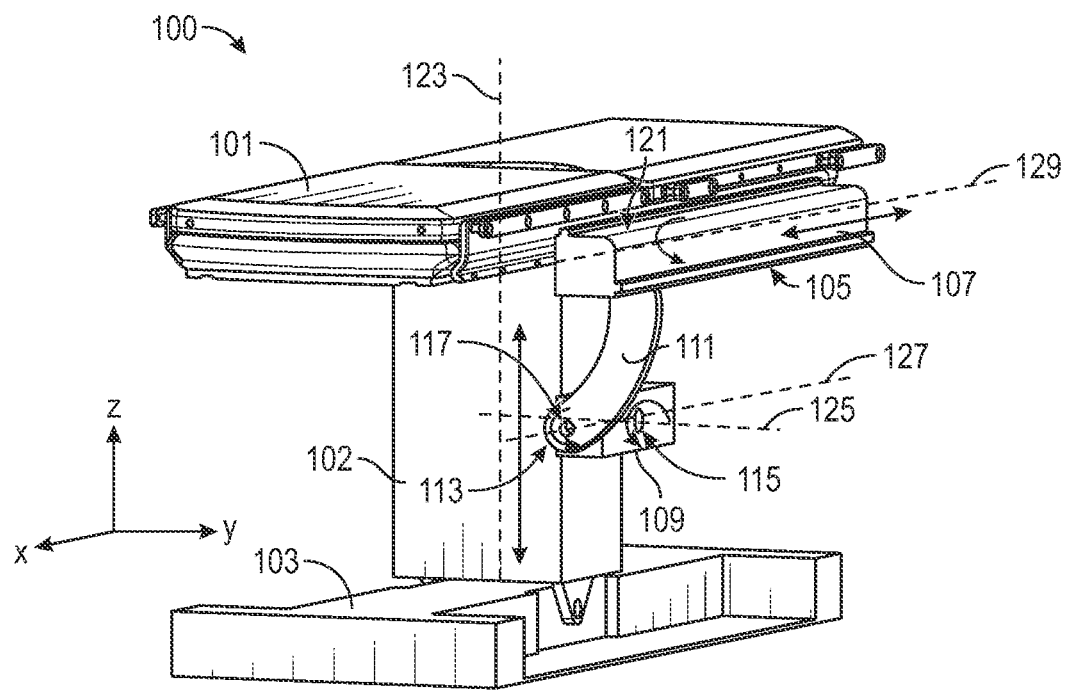
FIG. 12 illustrates an alternative embodiment of a table-based robotic system.
Figure 13:
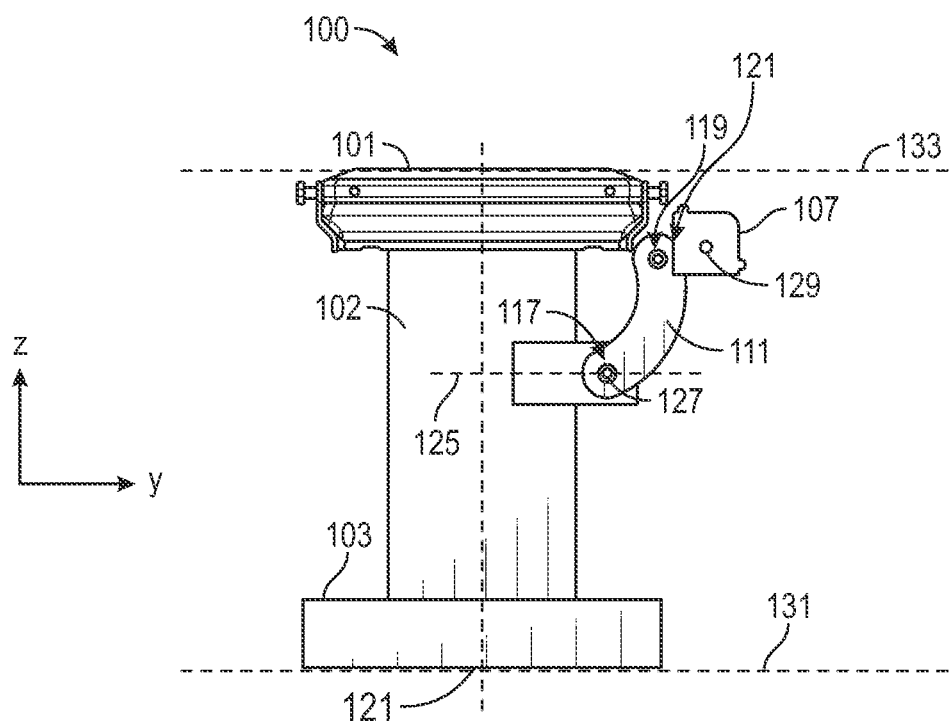
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift (e.g., vertical translation), lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
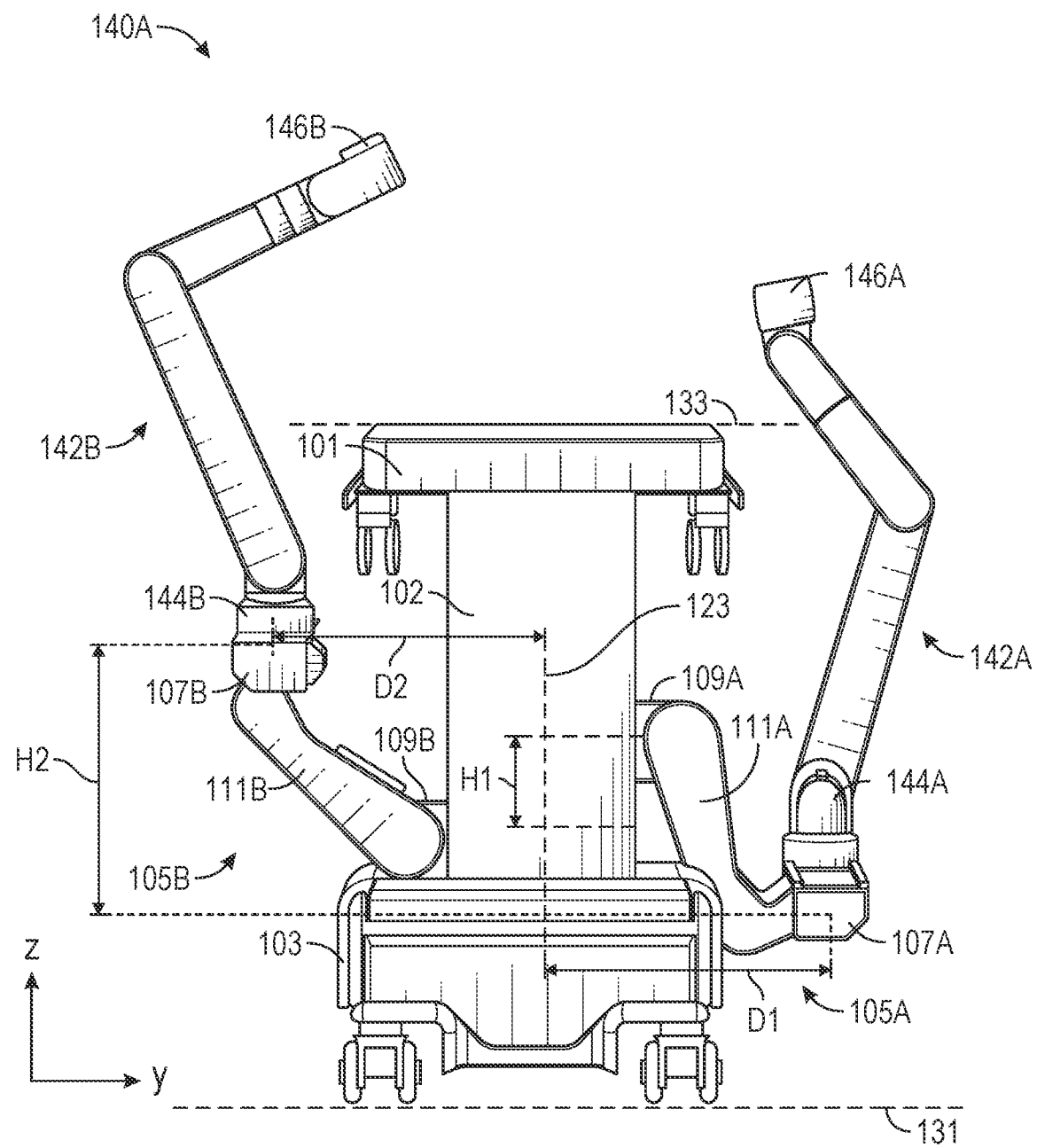
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
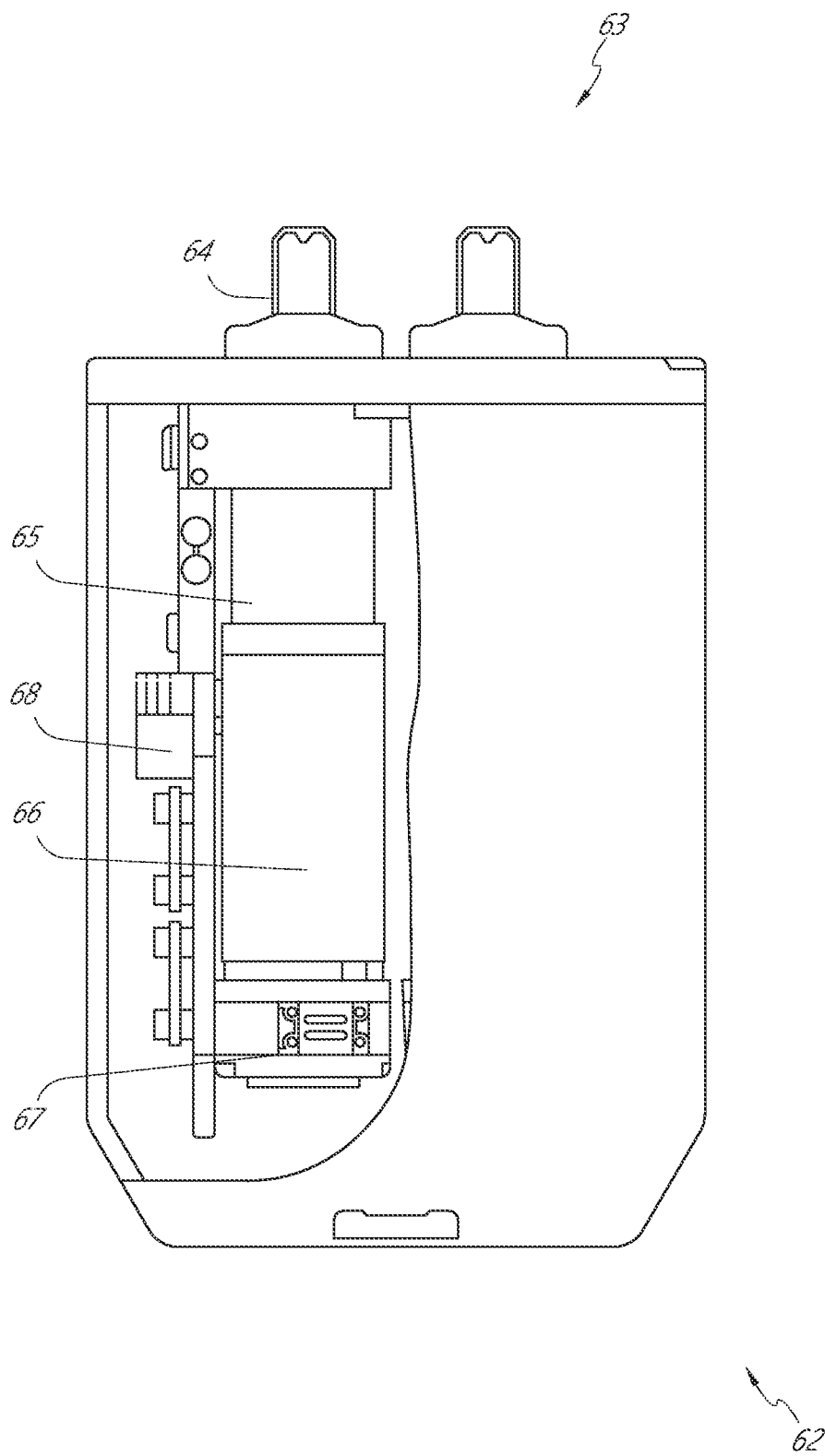
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
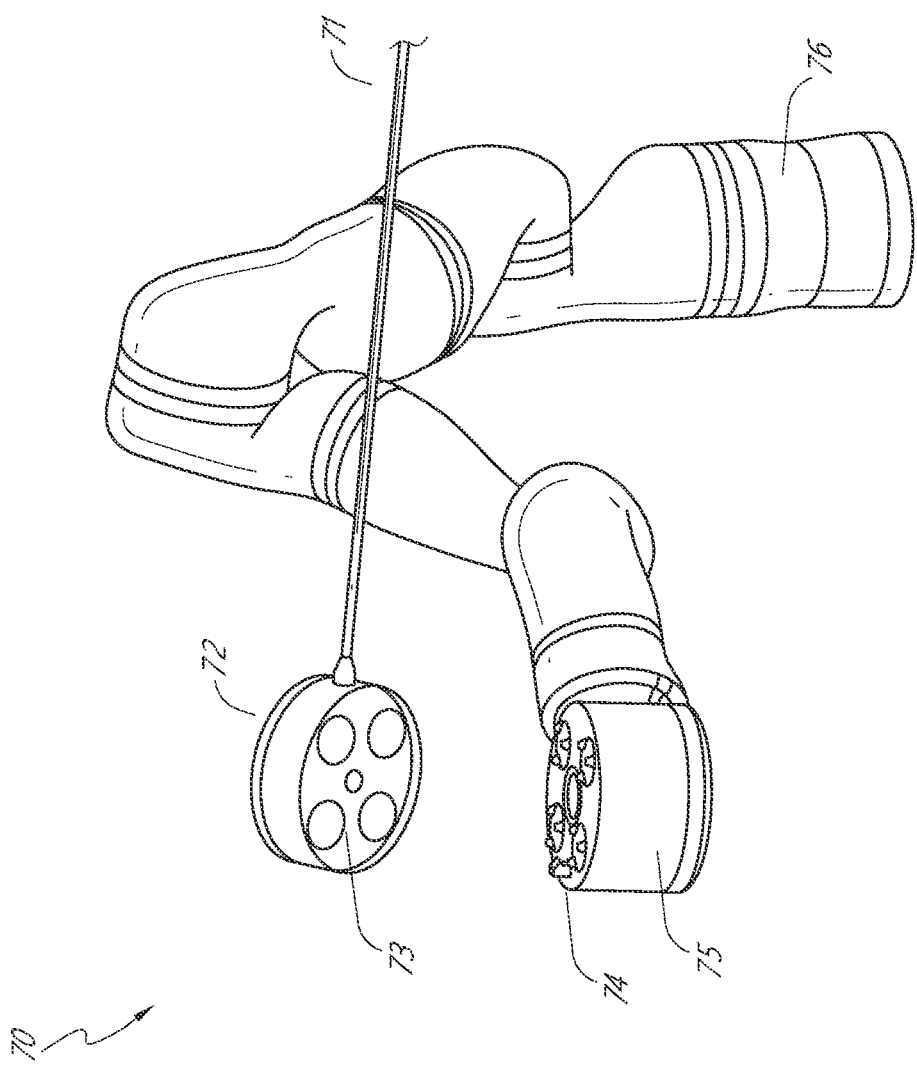
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
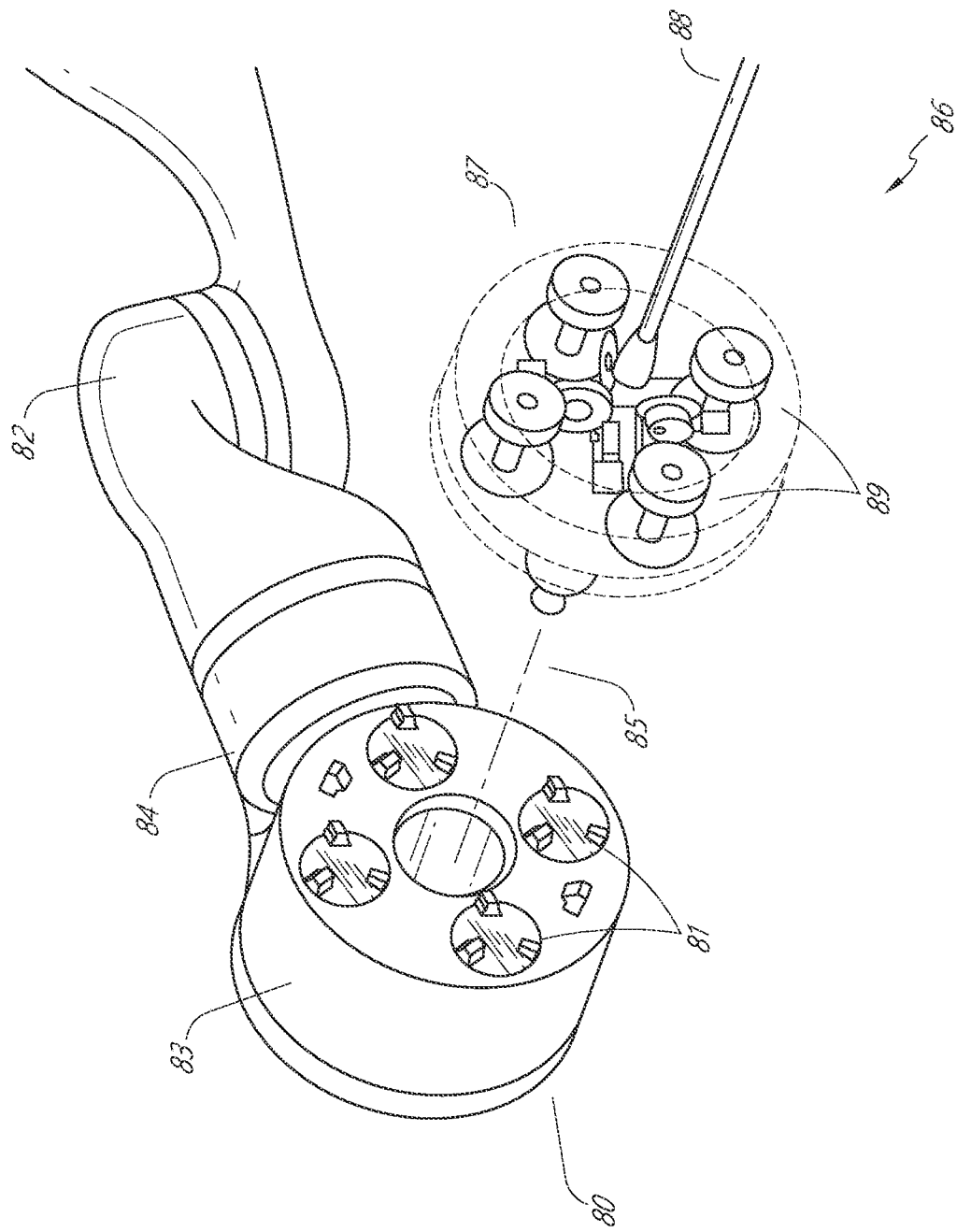
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
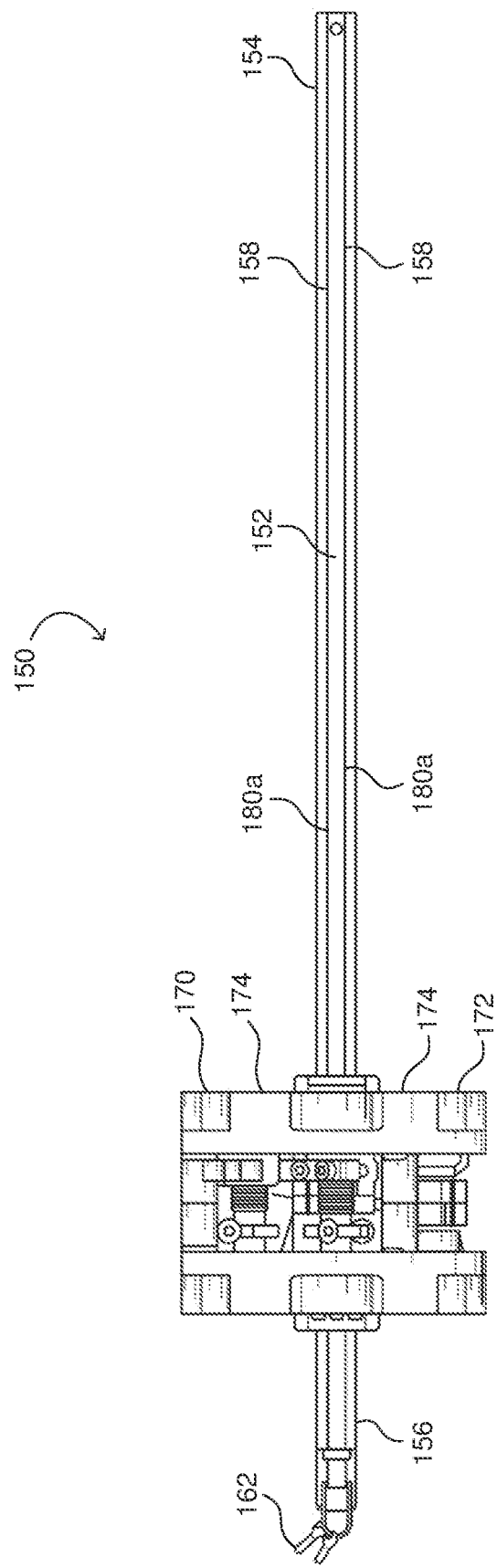
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
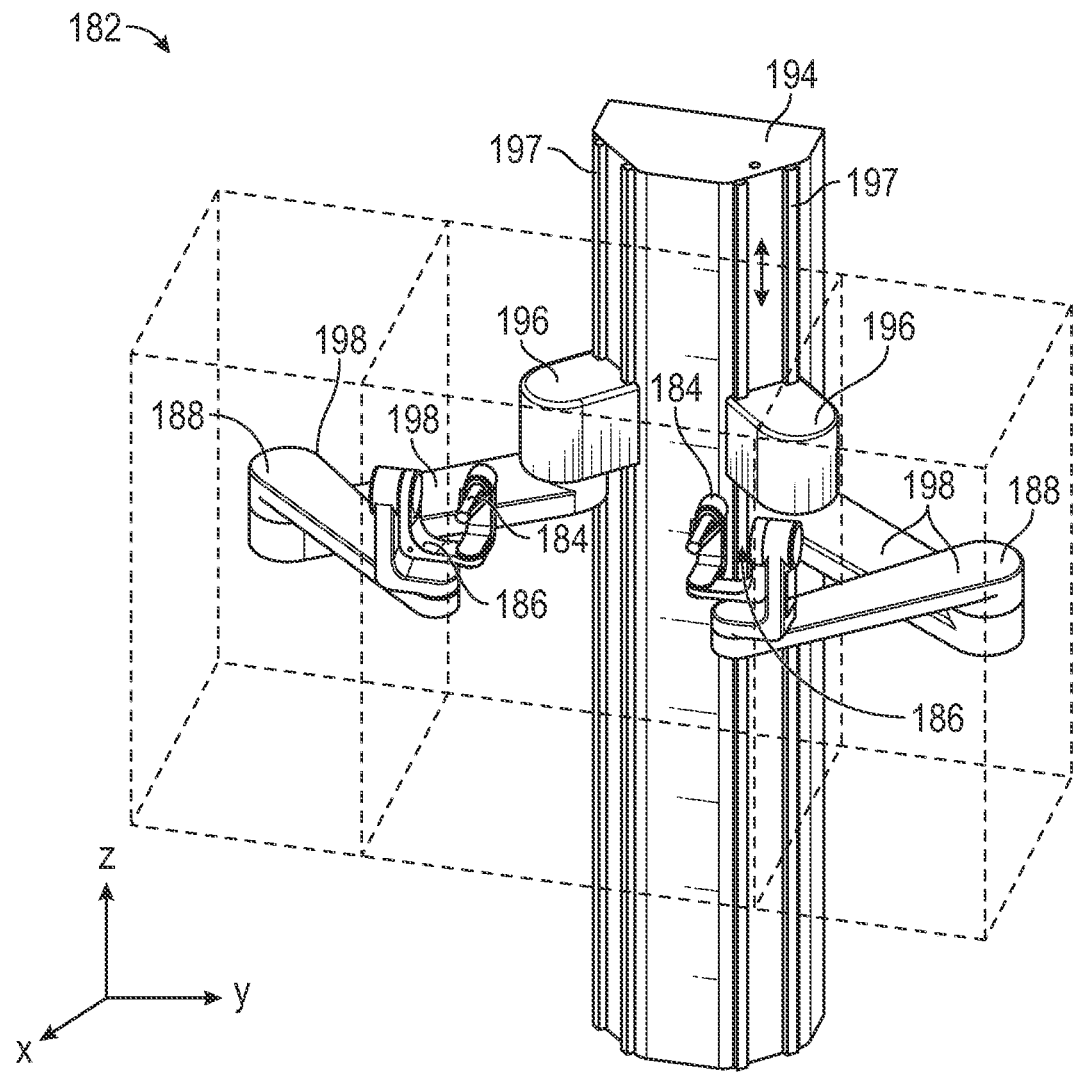
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
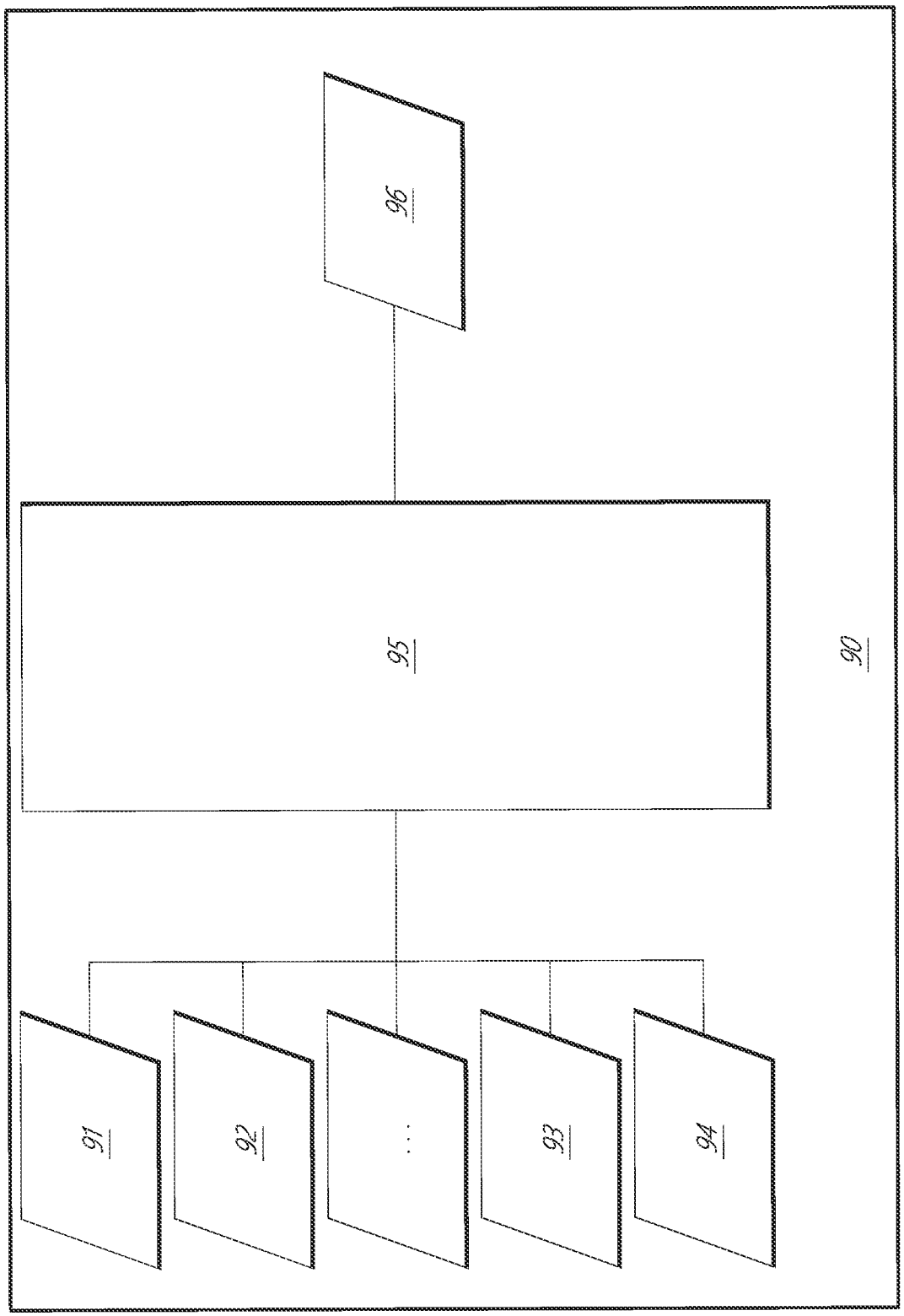
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Robotically Assisted Concomitant Procedures

The treatment of certain medical conditions may involve performing two or more medical procedures to fully treat the medical condition. For example, the diagnosis and management of pulmonary lesions may involve multiple treatment episodes to perform medical procedures including flexible endoscopy and thoracoscopy. After the discovery of a lesion from a radiographic study, such as via analysis of a CT scan, a physician may perform an endoscopic diagnosis and subsequent therapy over the course of multiple treatment episodes. In one example, if a physician suspects his or her patient has early stage cancer, the physician may order that the patient first undergo an endoscopic procedure for diagnosis of the cancer. During the endoscopic procedure, a nodule may be biopsied and, if the physician determines that removal of the nodule is necessary, the physician may order that patient undergo a second treatment episode for surgical resection of the nodule.

There are drawbacks to performing multiple treatment episodes. The clinical costs and time demands from both the care givers and patients are increased for such a multi-episode approach to diagnosing and treating a condition of the patient. Additionally, during the surgical resection procedure, a procedure (e.g., endoscopy) may need to be repeatedly performed to aid in accurately localizing the tumor and providing an operative target for surgical resection. Further, when staging medical procedures over multiple treatment episodes, patients may have to undergo multiple anesthetic episodes, which can carry increased risk and inconvenience to patients. And multiple treatment episodes may utilize increased perioperative resources (e.g., preoperative workup, postoperative recovery, and perhaps overnight hospital stays), thereby leading to increased time and costs to both the patient and the physician.

Rather than staging the medical procedures across multiple treatment episodes, the physician has the option of performing multiple procedures in serial fashion during a single treatment episode. Such a single treatment episode can be performed by calling upon additional clinical providers to assist in performing procedures in parallel as part of the single treatment episode.

However, as for multiple treatment episodes, there are drawbacks associated with single treatment episodes as they are currently performed. As noted above, multiple clinical providers may need to assist in performing a single treatment episode, thereby leading to increased costs and an overcrowded space in the operating room. Furthermore, to perform multiple procedures serially over a single treatment episode, the physician may alternate between the various approaches, which may involve switching between sterile and non-sterile techniques. Switching between sterile and non-sterile techniques may further involve changing attention from one surgical site to another, regowning, and significantly interrupted clinical workflow.

The coordination of multiple healthcare providers and/or physicians to perform procedures in parallel during a single treatment episode is expensive and may be cost prohibitive for certain procedures. One example of the use of multiple clinical providers in performing parallel procedures as part of a single treatment episode is Combined Endoscopic and Laparoscopic Surgery (CELS), which is a manual method of performing colonic polyp resection. Polyps can be evaluated as to whether they can be removed endoscopically based on their size, type, and location. When polyps cannot be removed endoscopically, they can be removed via segmental colectomy, which is accompanied with a comparatively high complication rate and increased recovery time. CELS was proposed as a method to enable extraluminal mobilization of the colon (with laparoscopic instruments) to make the polyp easier to resect intraluminally (with endoscopic instruments). CELS typically requires at least two physicians (to control the laparoscopic and endoscopic instruments respectively) and two assistants (to hold the laparoscope and colonoscope respectively). While one physician is moving an instrument, the remaining providers may hold their instruments still, which may be physically demanding over extended periods of time. There may be additional staff members in the room to assist with instrument exchange, pass suture or gauze, handle specimens after removal, and control laparoscopic instruments, etc.

Embodiments of the disclosure relate to systems and methods for performing two or more types/modes of procedures concomitantly (e.g., by a single user or team) as part of a single treatment episode. The systems and methods described herein improve upon the single and multiple treatment episodes described above. In some embodiments, parallel procedures can be performed as part of a single treatment episode with the aid of a novel robotic medical system, thereby reducing the need to have as many healthcare providers and/or physicians as with non-robot assisted parallel medical procedures, such as, e.g., existing CELS procedures.

In addition to the above example of endoscopic diagnosis and surgical resection of a cancerous tumor, other example medical procedures may benefit from the systems and methods described herein, including bronchoscopic localization of lung cancer with simultaneous thoracoscopic resection, endoscopic localization of gastrointestinal cancer with laparoscopic resection, endoscopic localization and resection of gastrointestinal cancer with laparoscopic assistance, endoscopic imaging or visualization for gastrointestinal reconstructive procedures, such as gastrectomy, roux-en-y-gastric bypass, etc., ureteroscopic stone/tumor localization and percutaneous removal/resection. In some embodiments, such procedures can be performed in a single treatment episode. In some embodiments, such procedures can be performed with a minimal number of clinicians, and in some cases, a single physician. Furthermore, in some embodiments, simultaneous procedures can be performed using a single type of console to control the simultaneous procedures.

In accordance with aspects of this disclosure, a first type of procedure performed during concomitant/parallel medical procedures can involve delivering one or more flexible devices into a patient, while a second type of procedure can involve delivering one or more rigid devices into the patient. For example, in one embodiment, the two concomitant procedures can involve an endoscopic procedure (e.g., using a flexible scope) in combination with a laparoscopic procedure (e.g., using a rigid scope). In a medical treatment involving a tumor in the bronchial tract, a first endoscopic tool (e.g., a flexible bronchoscope) can be inserted through the bronchial tract, while a second laparoscopic tool (e.g., a rigid camera or a cutter) can be inserted through an incision that provides access to the tumor.

In some embodiments, the first type of procedure can be performed through a natural orifice while the second type of procedure can be performed through an incision. For example, in a medical procedure involving the removal of kidney stones, a first tool (e.g., a laser) can be inserted through the natural orifice of the urethra to break up the stones in the renal pelvis, while a second tool (e.g., a vacuum) can be inserted percutaneously through an incision to suction and remove the broken kidney stones.

A. Systems and Methods for Performing Concomitant Procedures.

Figure 21:
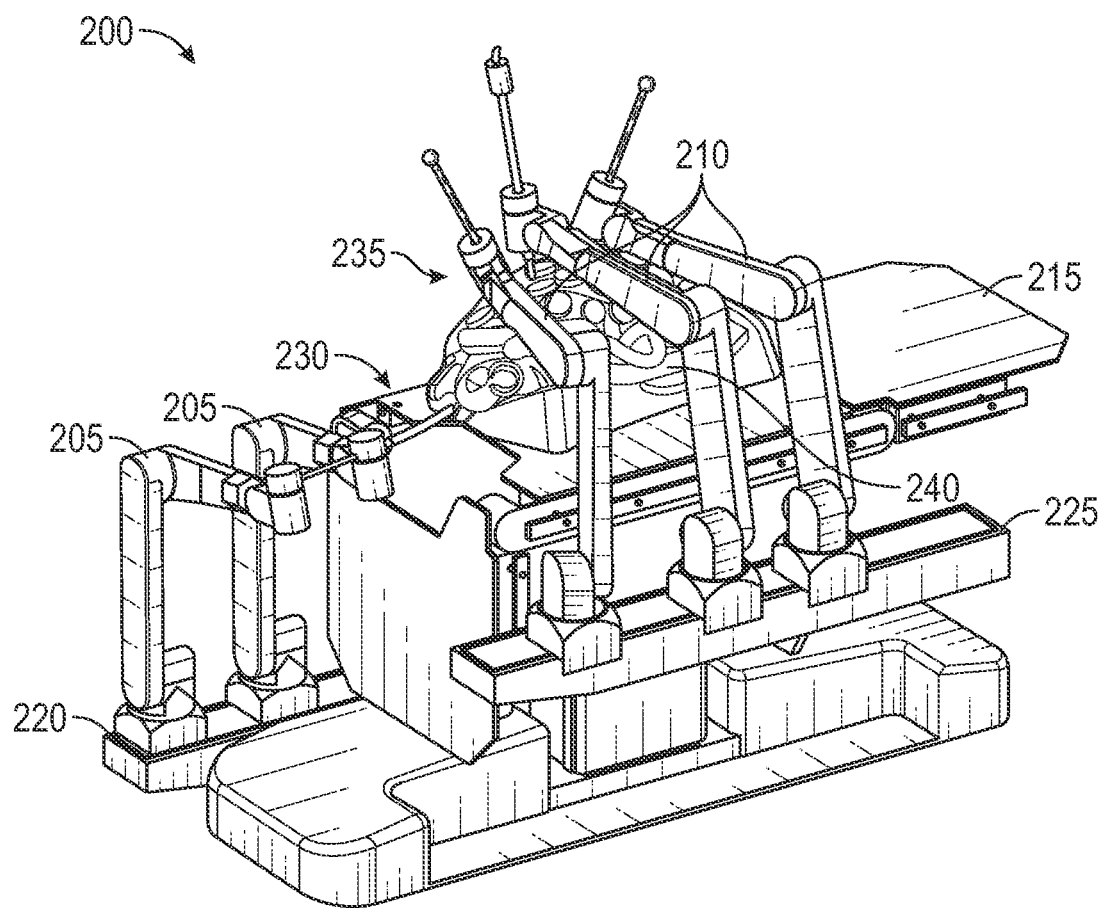
FIG. 21 illustrates an embodiment of a bed-based robotic system configured for performing concomitant procedures in accordance with aspects of this disclosure.

In some embodiments, a single robotic medical system can perform two or more types of medical procedures concomitantly as part of a single treatment episode. FIG. 21 illustrates an embodiment of a bed-based robotic system configured for performing concomitant procedures in accordance with aspects of this disclosure. As shown in FIG. 21, the robotic medical system 200 includes a first set of one or more robotic arms 205 and a second set of one or more robotic arms 210. The system 200 further includes a platform 215, which may include a bed onto which a patient can be positioned, with the first and second sets of robotic arms 205 and 210 positioned on bilateral arm supports or rails with respect to the platform 215. The first set of robotic arms 205 may be coupled to a first adjustable arm support 220 while the second set of robotic arms 210 may be coupled to a second adjustable arm support 225, located on an opposing side of the platform 215 with respect to the first adjustable arm support 220. The bed of the platform 215 may include a head portion and a foot portion. The first arm support 220 and the second arm support 225 may be positioned in between the head portion and the foot portion. The first arm support 220 and the second arm support 225 can also be configured to move relative to the platform 215 such that at least a portion of the first arm support 220 and/or the second arm support 225 extends beyond the head portion or the foot portion.

In certain embodiments, the first set of arms 205 may be configured to control one or more flexible instruments 230, such as, e.g., a colonoscope, bronchoscope or ureteroscope (e.g., having an inner and outer catheter), as part of an endoscopic procedure. The second set of arms 210 may be configured to control one or more rigid instruments 235, such as a rigid camera, vessel sealers, tissue cutters, staplers, needle drivers, etc., as part of a laparoscopic procedure. In the present embodiment, the first set of arms 205 are aligned in a virtual rail to deliver a flexible ureteroscope in accordance with some embodiments. The second set of arms 210 deliver one or more laparoscopic instruments through laparoscopic ports. In some embodiments, at least one of the laparoscopic instruments can be rigid, although in some embodiments, the second set of arms 210 can be configured to deliver a combination of rigid and flexible instruments, such as a rigid cutter and a flexible articulating laparoscope. As shown in FIG. 21, the first set of arms 205 is configured to approach the patient from a direction that is different from the second set of arms 210. For example, the first set of arms 205 can approach the patient from a base of the platform 215, while the second set of arms 210 can approach the patient from a side of the platform 215. In some embodiments, one or more of the endoscopic or laparoscopic instruments can be navigated in part or wholly via EM or fluoroscopic navigation. In some embodiments, the first set of arms 205 is capable of being locked while the second set of arms 210 is moveable. In other embodiments, the first set of arms 205 is moveable while the second set of arms 210 is locked.

As shown in the figure, the first set of arms 205 is coupled to the first adjustable arm support 220, while the second set of arms 210 is coupled to the second adjustable arm support 225. The first adjustable arm support 220 can be independently adjustable from the second adjustable arm support 225. In some embodiments, the first adjustable arm support 220 is at a height that is different from the second adjustable arm support 225, while in other embodiments, the first adjustable arm support 220 is at a height that is the same as the second adjustable arm support 225. In some embodiments, the arm supports 220, 225 and/or the arms 205, 210 can be stowed beneath the platform 215. In some embodiments, one or more of the arm supports 220, 225 and/or the arms 205, 210 can be elevated above a base of the platform, thereby avoiding "mop slop" and inadvertent dirt from getting on these components. In some embodiments, one or more arm supports 220, 225 and/or the arms 205, 210 can be elevated from a stowed position to a height that is higher than a top surface of the bed or platform 215.

In the present embodiment, a pair of arms 205 are coupled to the first adjustable arm support 220, while a trio of arms 210 are coupled to the second adjustable arm support 225. In other embodiments, the number of arms on each of the adjustable arm supports can be even. In other embodiments, the number of arms can be greater or less than the number of arms shown in FIG. 21.

Figure 22:
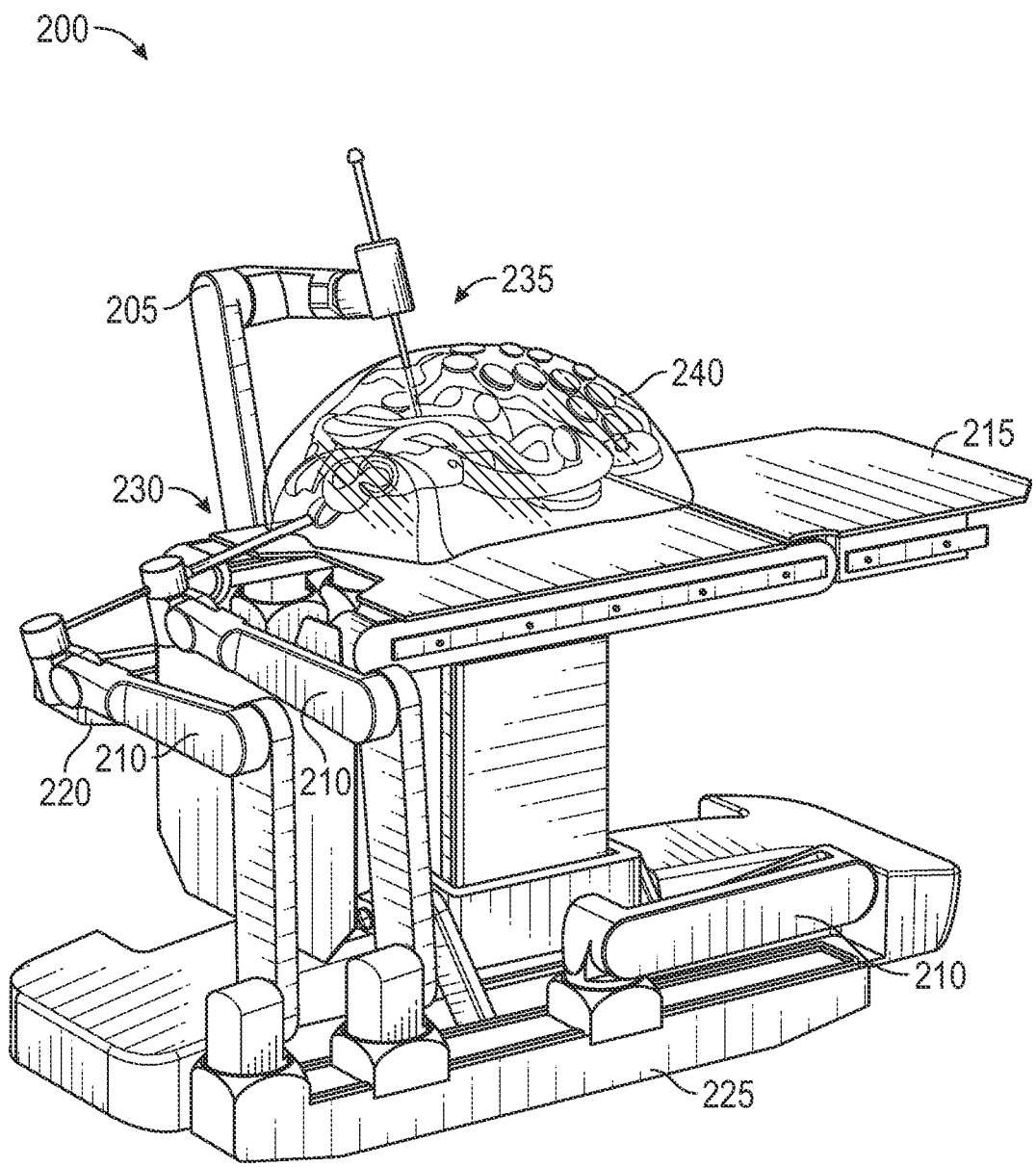
FIG. 22 illustrates another embodiment of a bed-based robotic system configured for performing concomitant procedures in accordance with aspects of this disclosure.

FIG. 22 illustrates another embodiment of a bed-based robotic system configured for performing concomitant procedures in accordance with aspects of this disclosure. Similar to the embodiment of FIG. 21, the embodiment illustrated in FIG. 22 includes a first set of one or more robotic arms 205, a second set of one or more robotic arms 210, a platform 215 with the plurality of robotic arms 205 and 210 positioned on bilateral arm supports with respect to the platform 215. These bilateral arm supports include a first adjustable arm support 220, and a second adjustable arm support 225.

In contrast to the embodiment illustrated in FIG. 21, in the FIG. 22 embodiment, the first set of robotic arms 205 comprises a single robotic arm that is configured to control a rigid laparoscopic instrument 235 percutaneously through a patient while the second set of robotic arms 210 comprises a pair of robotic arms that are configured to control a flexible endoscopic instrument 230. In other embodiments, the robotic arms 205 and 210 may be located on the same side of the bed (or adjacent sides of the bed) and may be configured to control a flexible endoscopic instrument 230 and a rigid laparoscopic instrument 235, respectively. In still other embodiments, a set of robotic arms 205 and 210 including at least one arm located on each side of the platform 215 may be configured to control a first medical instrument (e.g., a flexible endoscopic instrument 230), which another set of robotic arms 205 and 210 including at least one arm located on each side of the platform 215 may be configured to control a second medical instrument (e.g., a rigid laparoscopic instrument 235).

In each of the embodiments illustrated in FIGS. 21 and 22, a single bed-based system having robotic arms attached thereto can be configured to perform both an endoscopic procedure involving one or more flexible instruments 230, as well as a laparoscopic procedure involving one or more rigid instruments 235. The endoscopic procedure can be performed through a natural orifice (e.g., a throat), while the laparoscopic procedure can be performed through an incision (e.g., a chest). The procedures can advantageously be performed concurrently/concomitantly (partially or wholly) via a single console (additional details of which are provided below) by a single user. In some embodiments, the robotic medical system 200 can be configured to perform two types of medical procedures in series as well if desired. For example, a first type of procedure may be performed on a patient. If such a procedure is ineffective on its own, a second type of procedure can be performed to overtake or supplement the first type of procedure as part of a "procedure escalation."

In each of FIGS. 21 and 22, the robotic arms 205 and 210 can be stowed and subsequently deployed from underneath the platform 215. The robotic arms 205 and 210 are configured to be positioned in multiple locations e.g., near a patient's 240 feet and/or near a patient's 240 right side based on commands received from a user. The robotic arms 205 and 210 are configured to be translatable along the adjustable arm supports 220 and 225. The robotic arms 205, 210 are capable of multiple degrees of freedom, including two, three, four, five, six, seven, eight or greater. In some embodiments, the robotic arms 205, 210 include one or more redundant degrees of freedom. The robotic arms 205, 210 are coupled to adjustable arm supports 220, 225 that are configured to provide vertical, lateral, and longitudinal adjustment of the robotic arms 205 and 210. Independent of the movement of the robotic arms 205 and 210, in some embodiments, the adjustable arm supports are configured to be adjusted in three degrees of freedom. In certain embodiments, the adjustable arm supports 220 and 225 may be in the form of bars or rails, along which the bases of the robotic arms can translate. The bases may couple the robotic arms 205 and 210 to the adjustable arm supports 220 and 225.

Referring to the specific configuration of the robotic system illustrated in FIG. 21, the first adjustable arm support 220 has been adjusted horizontally such that it extends below and beyond a base of the platform 215, thereby allowing the first robotic arms 205 to be positioned near the patient's 240 feet as part of an endoscopic procedure. The second adjustable arm support 225 has been kept substantially aligned with the platform 215, but has been adjusted vertically such that the second robotic arms 210 attached thereto can be positioned above the patient 240 as part of a laparoscopic procedure. The first and second adjustable arm supports 220 and 225 allow the robotic arms 205 and 210 to approach from different directions, including different heights and lateral positions.

Although the robotic arms 205 and 210 have been described as divided into a first set of robotic arms 205 and a second set of robotic arms 210, the robotic arms 205 and 210 can be divided into other groupings (including sets of one or more arms), each configured to perform a distinct procedure as part of a concomitant medical procedure. In some embodiments, a concomitant procedure (e.g., for diagnosis) can be performed with as few as two arms-one to hold a flexible camera, the other to hold an instrument. In some embodiments, a concomitant procedure (e.g., for treatment) can be performed with two arms or three arms. In some embodiments, four or more robotic arms 205 and 210 can be provided.

Depending on the combination of medical procedures being performed concomitantly, the robotic arms 205 and 210 can be configured and/or operated to control various medical instruments. Examples of uses for which one or more of the robotic arms 205 and 210 can be implemented using the robotic medical system 200 include: (i) a robotic arm configured to control an introducer or sheath which provides access to a natural body orifice, such as, e.g., the nose, mouth, vagina, urethra, rectum, or ear; (ii) a robotic arm configured to control an endoscope and/or endoscopic instrumentation (e.g., a flexible instrument) through a natural orifice into the body, with or without the aforementioned introducer or sheath; (iii) a robotic arm configured to hold and command a thoracoscopic or laparoscopic camera (e.g., a flexible or rigid device) which provides extraluminal visualization in the relevant anatomic space (e.g., thoracic, abdominal, extra-peritoneal, and/or retro-peritoneal space); and/or (iv) one or more robotic arms configured to hold and command thoracoscopic or laparoscopic instrumentation (e.g., a rigid device). These are just exemplary uses, and one skilled in the art will appreciate that the systems described herein are not limited to these practices.

There are a number of advantages in using a single system such as the robotic medical system of one of FIGS. 21 and 22 to perform concomitant endoscopic and laparoscopic procedures with flexible and rigid tools. First, the use of a single system conserves the amount of space occupied by the components of the system by having less equipment/capital in the operating room. Second, the use of a single system makes it easier for a single clinician/physician to perform both types of procedures without the aid of other clinicians/physicians within the operating room. And third, with the use of a single system, each of the robotically controllable components of the system may be tied to the same global reference frame—e.g., position(s) and/or orientation(s) of the endoscopic instrument(s) can be easily referenced relative to position(s) and/or orientation(s) of the laparoscopic instrument(s). In other words, a single system provides knowledge of positional and/or orientation-related data for all instruments and manipulators relative to a single coordinate frame, thereby enabling features such as collision prevention and/or avoidance, and/or computer-generated displays of instruments with respect to each other.

Figure 23:
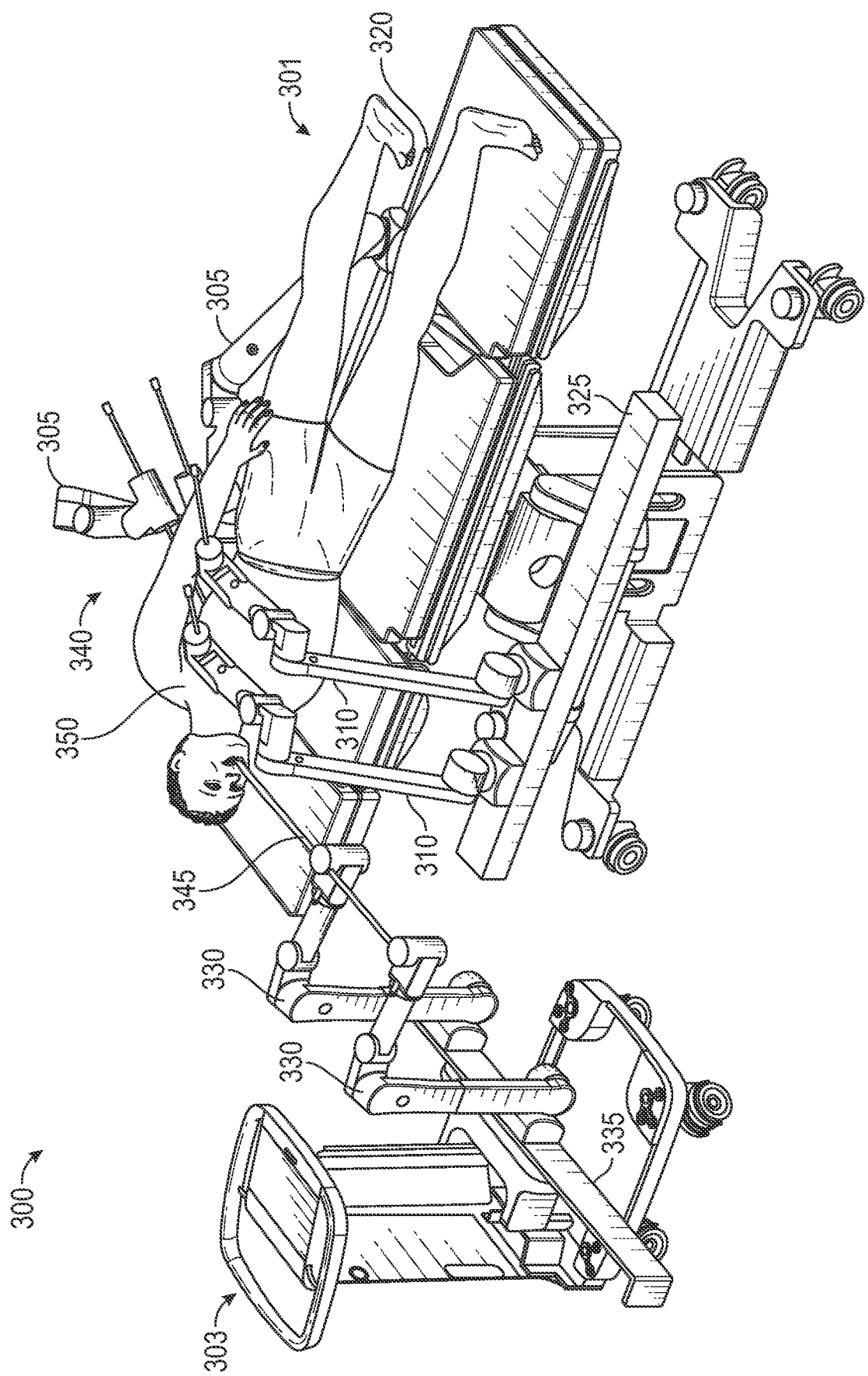
FIG. 23 illustrates yet another embodiment of a robotic system configured for performing concomitant procedures in accordance with aspects of this disclosure.

FIG. 23 illustrates yet another embodiment of a robotic system configured for performing concomitant procedures in accordance with aspects of this disclosure. The robotic medical system 300 includes both a platform-based robotic system 301 and a cart-based robotic system 303. The platform-based robotic system 301 includes a first set of one or more robotic arms 305, a second set of one or more robotic arms 310, and a bed or platform 315, wherein the plurality of robotic arms 305 and 310 are positioned bilaterally with respect to the platform 315. The system 300 further includes a first adjustable arm support 320 coupled to the first set of one or more robotic arms 305, and a second adjustable arm support 325 coupled to the second set of one or more robotic arms 310. The cart-based robotic system 303 includes a third set of one or more robotic arms 330 coupled to a third adjustable arm support 335. In the present embodiment, the platform-based robotic system 301 and the cart-based robotic system 303 are advantageously integrated to perform concomitant procedures as part of a single treatment episode.

The first and second sets of robotic arms 305 and 310 are configured to control one or more rigid instruments 340, such as, e.g., a camera, vessel sealers, tissue cutters, staplers, needle drivers, etc., as part of a laparoscopic procedure performed on a patient 350. The third set of robotic arms 330 are configured to control one or more flexible instruments 345, such as, e.g., a colonoscope, bronchoscope or ureteroscope (e.g., having an inner and outer catheter), as part of an endoscopic procedure. However, in other configurations, any combination or subset of the first, second, and third robotic arms 305, 310, and 330 may be configured to control a rigid instrument 340 and/or a flexible instrument 345. In some embodiments, the robotic system 300 may include two or more cart-based systems 303, each of which may be configured to control one or more medical instruments.

Figure 24:
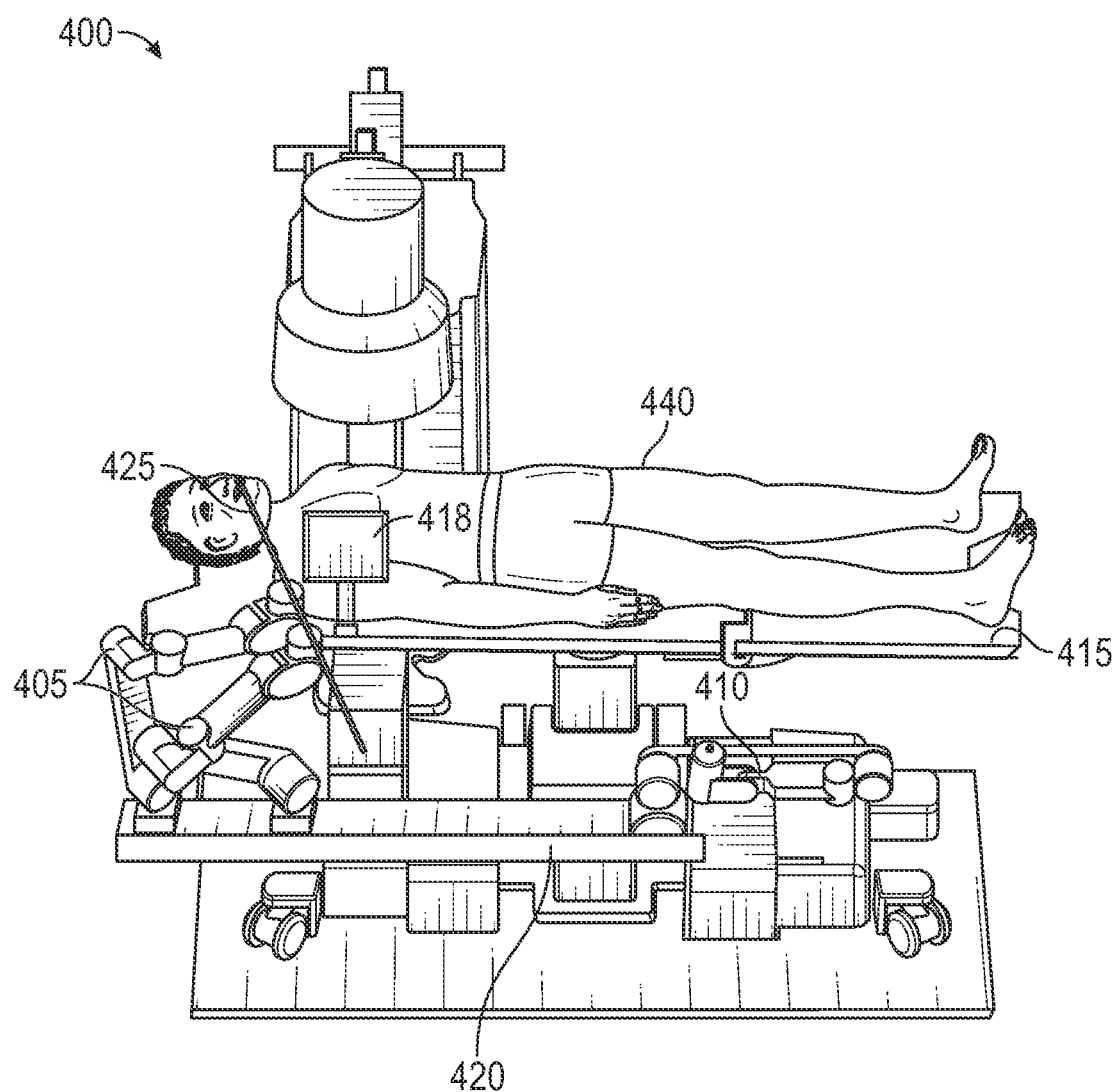
FIGS. 24 and 25 illustrate two configurations of another embodiment of a bed-based robotic system configured for performing concomitant procedures in accordance with aspects of this disclosure.
Figure 25:
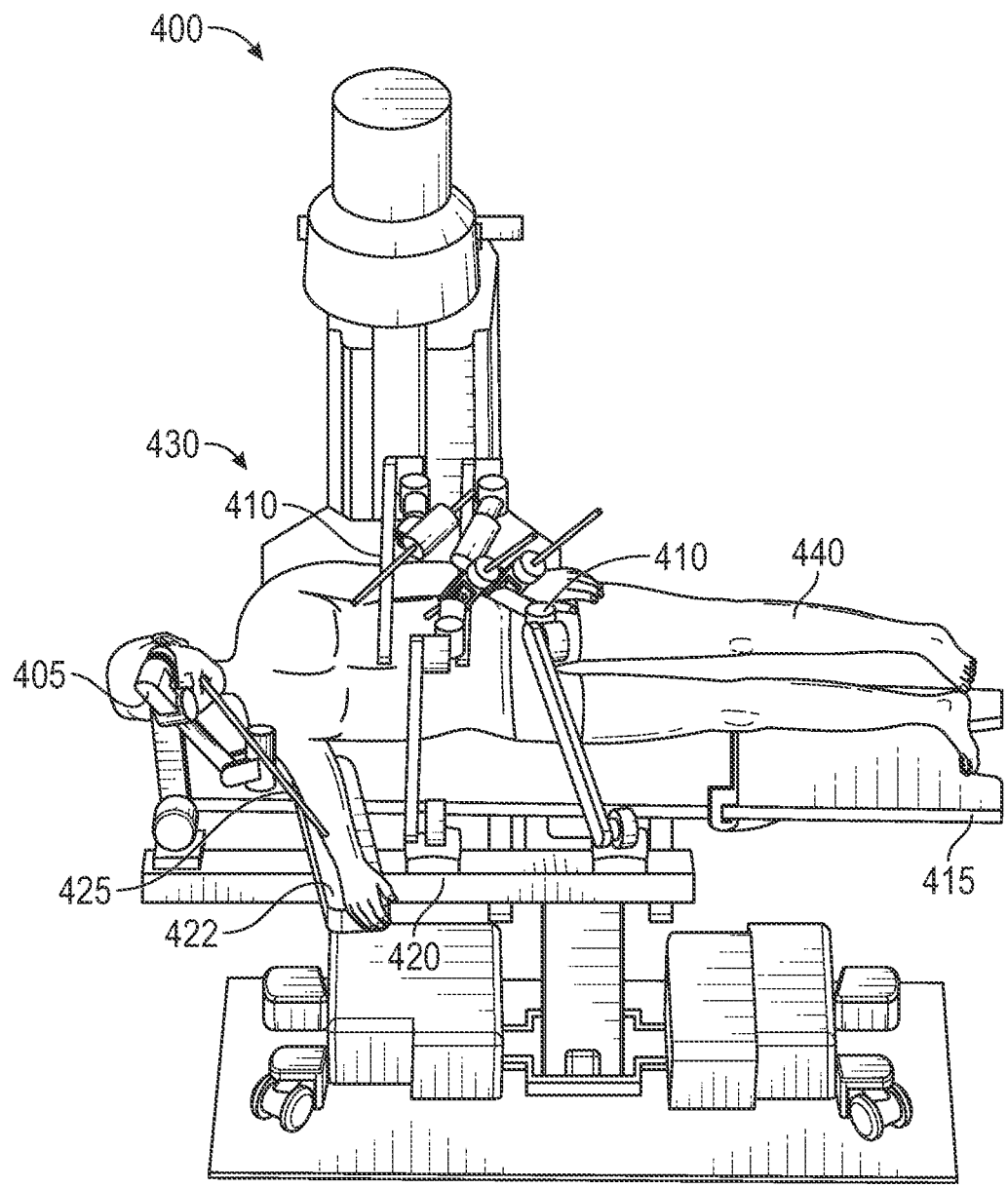

FIGS. 24 and 25 illustrate two configurations of another embodiment of a bed-based robotic system configured for performing concomitant procedures in accordance with aspects of this disclosure. As shown in FIGS. 24 and 25, the robotic medical system 400 includes a first set of one or more robotic arms 405, a second set of one or more robotic arms 410, a platform 415, an adjustable arm support 420, one or more flexible medical instruments 425, and one or more rigid medical instruments 430. In the present embodiment, the first set of one or more robotic arms 405 and the second set of one or more robotic arms 410 share the same adjustable arm support 420. An imaging device (e.g., CT, fluoroscopic, etc.) is positioned on a side of the platform 415 opposite the arm support 420. The system 400 further includes an electromagnetic field generator 418 for assisting in navigation of one or more instruments via EM sensor.

In a first configuration of the robotic medical system shown in FIG. 24, the first set of robotic arms 405 can be configured to control a flexible medical instrument 405 to be inserted through a patient's 440 bronchial tract. The second set of robotic arms 410 can be stowed below the platform 415 without controlling a medical instrument. In a second configuration shown in FIG. 25, the first set of robotic arms 410 can be configured to control the flexible instrument 425 while the second set of robotic arms 410 have been elevated from the stowed position to control one or more rigid instruments 430, which can be inserted through an incision formed in the patient 440. The robotic arms can be elevated via the adjustable arm supports 420. As shown in FIG. 25, an arm rest 422 can be coupled to the platform and/or one or more of the adjustable arm supports 420 to allow a patient's arm to rest during a procedure. As can be seen in FIGS. 24 and 25, different subsets of the robotic arms 405 and 410 can be selected to control the medical instruments 425 and 430 depending on how the robotic medical system 400 is configured or utilized. In particular, two robotic arms 405 may be included as part of the first set of robotic arms 405 to control the flexible instrument in the configuration of FIG. 24, while a single robotic arm 405 can be included as part of the first set of robotic arms 405 to control the flexible instrument in the configuration of FIG. 25. As shown in FIGS. 24 and 25, different combinations of robotic arms 405, 410 on a given adjustable arm support 420.

Figure 26:
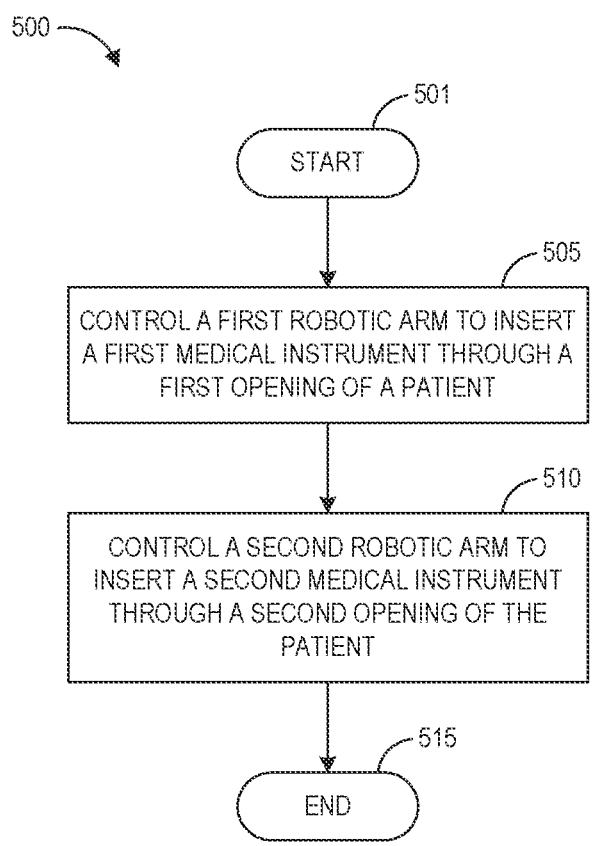
FIG. 26 is a flowchart illustrating an example method operable by a robotic system, or component(s) thereof, for performing concomitant medical procedures in accordance with aspects of this disclosure.

FIG. 26 is a flowchart illustrating an example method operable by a robotic system, or component(s) thereof, for performing at least partially or wholly concomitant medical procedures in accordance with aspects of this disclosure. For example, the steps of method 500 illustrated in FIG. 26 may be performed by processor(s) and/or other component(s) of a medical robotic system (e.g., robotically enabled system 10, or one of the robotic medical systems 200, 300, or 400 discussed above) or associated system(s). For convenience, the method 500 is described as performed by the "system" in connection with the description of the method 500.

The method 500 begins at block 501. At block 505, the system may control a first robotic arm to insert a first medical instrument through a first opening of a patient. At block 510, the system may control a second robotic arm to insert a second medical instrument through a second opening of the patient. The first robotic arm and the second robotic arm may be part of a first platform and the first opening and the second opening may be positioned at two different anatomical regions of the patient. The method 500 ends at block 515.

As an example implementation of the method 500 and with reference to the embodiment of FIG. 21, at block 505 the robotic medical system 200 may control the first set of robotic arms 205 to insert the flexible medical instrument 230 through a first opening of the patient 240. Similarly, at block 510 the robotic medical system 200 may control the second set of robotic arms 210 to insert the rigid medical instrument 230 through a second opening of the patient 240. In some embodiments, the first opening may be a natural orifice of the patient and the second opening may be an incision formed in the patient.

In some embodiments, the first medical instrument can comprise a first image capture device (e.g., an endoscope) and the second medical instrument can comprise a second image capture device (e.g., a laparoscope). By inserting the first and second medical instruments (each having a camera or other imaging component) through different openings positioned at two different anatomical regions of the patient, it is possible to provide different views of one or more anatomical regions of the patient. For example, when the flexible instrument is inserted through the patient's colon and the rigid instrument is inserted into the patient's abdominal cavity, the flexible instrument may be able to provide a view of a colon polyp from within the colon, while the rigid instrument may be able to provide a view of the same colon polyp from the abdominal cavity (e.g., from exterior of the colon). The system described herein advantageously allows a user to switch between the different camera views when viewing a display. In some embodiments, a view from the first image capture device can be overlaid on a view from the second image capture device on a display. In some embodiments, a view of the first image capture device can be placed side-by-side with the second image capture device in a tiled view on a display. Additional details regarding camera view manipulation are described below.

Aspects of this disclosure, including the method 500 of FIG. 26, may enable standalone endoscopic procedures, percutaneous procedures, laparoscopic procedures, as well as simultaneous combinations thereof. When utilizing all three modalities during a single procedure, a subset of one or more robotic arms can be allocated to drive and control flexible endoscopes and instrumentation to provide direct visualization and access to lumens in the body, another subset of one or more robotic arms can be allocated to drive and control laparoscopic/thoracoscopic cameras to provide direct visualization inside of various body cavities, while another subset of one or more robotic arms can be allocated to drive and control rigid, semi-rigid, or flexible instrumentation inside of a body cavity. The robotic arms can be configured and deployed as needed for any case.

Figure 27A:
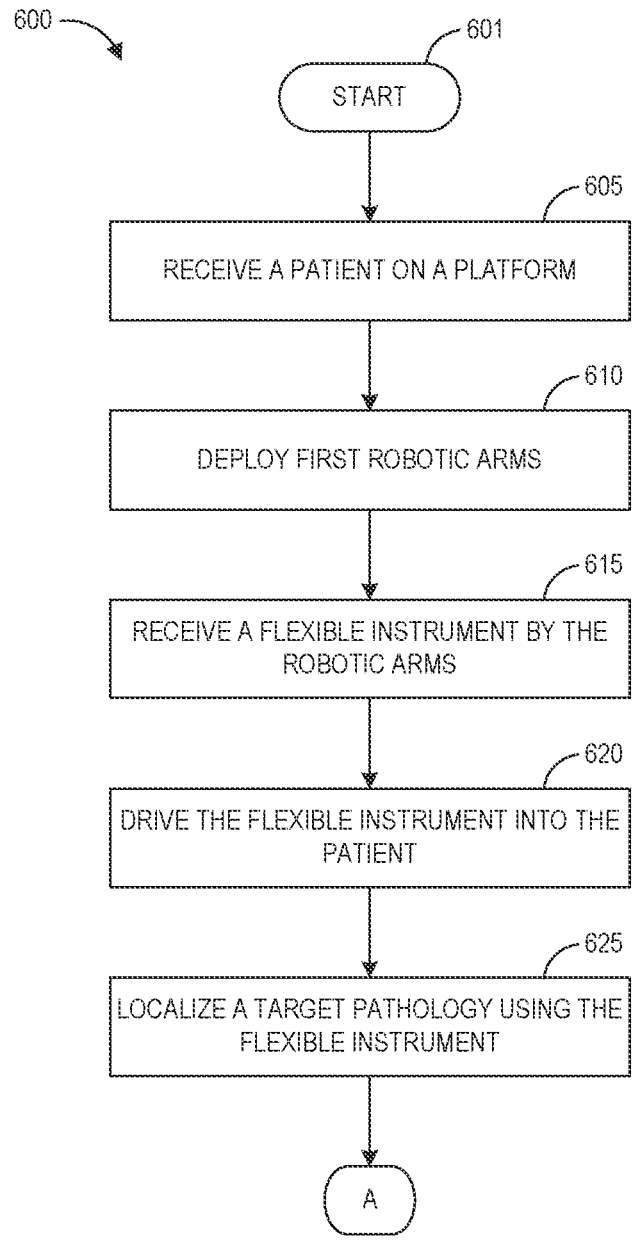
FIGS. 27A and 27B provide a flowchart illustrating another example method operable by a robotic system, or component(s) thereof, for performing concomitant endoscopic and thoracoscopic procedures in accordance with aspects of this disclosure.
Figure 27B:
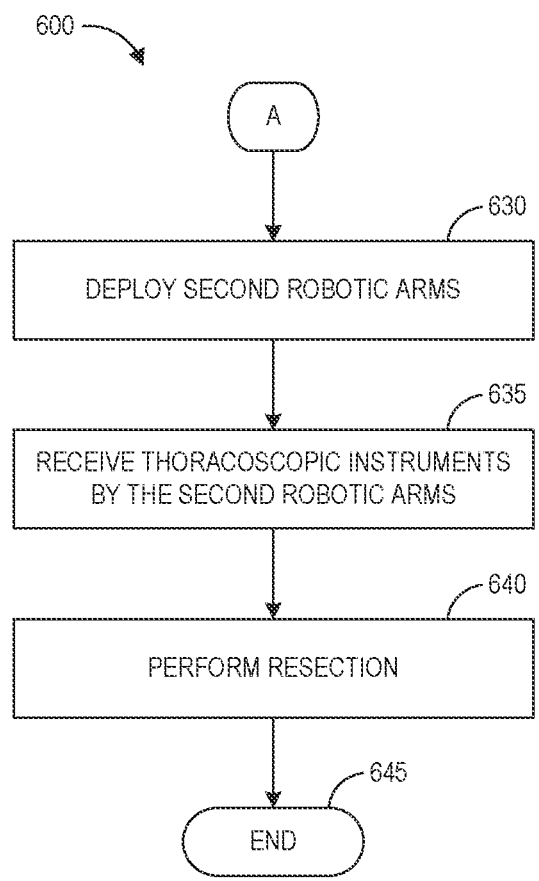

FIGS. 27A and 27B provide a flowchart illustrating another example method operable by a robotic system, or component(s) thereof, for performing concomitant endoscopic and thoracoscopic procedures in accordance with aspects of this disclosure. For example, the steps of method 600 illustrated in FIGS. 27A and 27B may be performed by processor(s) and/or other component(s) of a medical robotic system (e.g., robotically enabled system 10, or one of the robotic medical systems 200, 300, or 400) or associated system(s). For convenience, the method 600 is described as performed by the "system" in connection with the description of the method 600.

The method 600 begins at block 601. At block 605, a bed-based platform may be configured to receive a patient, transferred onto the bed by operating room staff. At block 610, the system may deploy first arms either from the bed or an integrated cart-based system in preparation for an endoscopic instrument. At block 615, the first robotic arms receive a flexible instrument, which may be loaded onto the first robotic arms by operating room staff. At block 620, under control of a physician, the system may drive the flexible instrument into the patient via a natural bodily orifice.

At block 625, the system may localize a target pathology using the flexible instrument. In the case of pulmonary lesions, blocks 620 and 625 may involve introducing the flexible instrument into the airway and driving the flexible instrument, under control of the physician, to the target (e.g., a lesion of interest).

At block 630, the system may deploy second robotic arms to perform laparoscopic resection. In some embodiments, block 630 may be performed in response to a determination that the pathology is cancerous. At block 645, the second robotic arms may receive thoracoscopic instruments, which may be loaded onto the first robotic arms by operating room staff. The operating room staff may also create thoracoscopic ports through which the thoracoscopic instruments are configured to be inserted into the patient. The thoracoscopic instrument may include a rigid camera, in this case a thoracoscope, and thoracoscopic instruments. The thoracoscopic ports may comprise cannulas which provide access to the patient's thoracic cavity.

At block 640, the system may perform laparoscopic resection of the target using the thoracoscopic instruments under control of the physician. The flexible instrument and the thoracoscope may provide separate views of the target from inside and outside of the airway, respectively, aiding the physician in performing the resection. Once resection is complete, the physician and/or operating room staff may remove the thoracoscopic instruments and close thoracoscopic ports and remove flexible device from the patient. The method 600 ends at block 645.

B. Procedure Escalation.

One benefit of the ability to control both endoscopic and laparoscopic instruments from a single platform (or a hybrid bed-based platform and cart-based system) is the ability to escalate the level of invasiveness of a surgical procedure as needed. Different procedures have different degrees of invasiveness. For example, a first type of procedure can be a purely endoscopic resection. A second type of procedure can be an endoscopic resection with laparoscopic assistance. And a third type of procedure can be a laparoscopic resection. The systems and methods described herein can advantageously enable a physician to escalate a procedure from one type of procedure to another with ease, such as from the first type of procedure to the second type of procedure, the second type of procedure to the third type of procedure, or from the first type of procedure to the third type of procedure.

In some embodiments, a physician may intend to perform the first type of procedure (e.g., purely endoscopic resection) and escalate treatment to include the second type of procedure (e.g., endoscopic resection with laparoscopic assistance). In some embodiments, the first type of procedure can be less invasive than the second type of procedure. For example, in the first type of procedure, a physician can attempt to perform a resection endoscopically without having to form an incision in a patient. In the second type of procedure, the degree of invasiveness increases as ports and holes are introduced in a patient's abdomen in order to provide laparoscopic assistance. The ports and holes can be provided to introduce a laparoscope and/or other laparoscopic instruments for e.g., viewing tissue and positioning; however, the resection is still endoscopic, which keeps complication rates and recovery time relatively minimal. The systems and methods described herein can advantageously enable a physician to escalate a procedure from the first type of procedure to the second type of procedure with ease.

In some embodiments, a physician may intend to perform the second type of procedure (e.g., endoscopic resection with laparoscopic assistance) and escalate treatment to include the third type of procedure (e.g., laparoscopic resection). In some embodiments, the second type of procedure can be less invasive than the third type of procedure. For example, in the second type of procedure, a physician can attempt to perform an endoscopic resection with laparoscopic assistance. In the third type of procedure, the degree of invasiveness increases as the resection is performed laparoscopically. Such a resection, such as a segmental colectomy, can involve higher risk and recovery time relative to the first and second types of procedures. The systems and methods described herein can advantageously enable a physician to escalate a procedure from the second type of procedure to the third type of procedure with ease.

One example treatment for which procedure escalation may be performed is colon polyp resection. A physician can begin a treatment by attempting a purely endoscopic resection of a colon polyp. If the purely endoscopic resection fails, the physician can quickly escalate to perform an endoscopic resection of the colon polyp with the assistance of laparoscopic instruments. In some embodiments, the escalation can be performed without bringing additional personnel or capital equipment into the room. If the endoscopic resection is still inadequate for resection despite the aid of laparoscopic instruments, the physician can escalate the procedure to a fully laparoscopic procedure and pursue a laparoscopic resection. In this example, performing an endoscopic resection with the assistance of laparoscopic instruments may have a higher level of invasiveness than performing a pure endoscopic resection, while performing a laparoscopic resection may have a higher level of invasiveness than performing an endoscopic resection with the assistance of laparoscopic instruments. The level of invasiveness of a given procedure may be determined based on numerous factors, including but not limited to the desired or expected recovery time of the patient, the absence or presence of an incision to deliver instrumentation, the size of an incision required to deliver the medical instruments into the patient's body, the expected morbidity after a procedure, the expected complication risk, etc.

By performing a treatment using procedure escalation, a physician can attempt to perform the least invasive procedure first, before attempting to perform more invasive procedures. For example, by treating the colon polyp using procedure escalation, the physician may advantageously be able to resect some or all of the colon polyp using a full endoscopic resection, before possibly moving on to more invasive procedures, thereby potentially reducing the associated recovery times for the patient without extending treatment over multiple episodes. Although procedure escalation is described above in connection with a colon polyp example, procedure escalation can be applied to other medical procedures including, for example, the diagnosis and resection of cancerous nodules.

Figure 28:
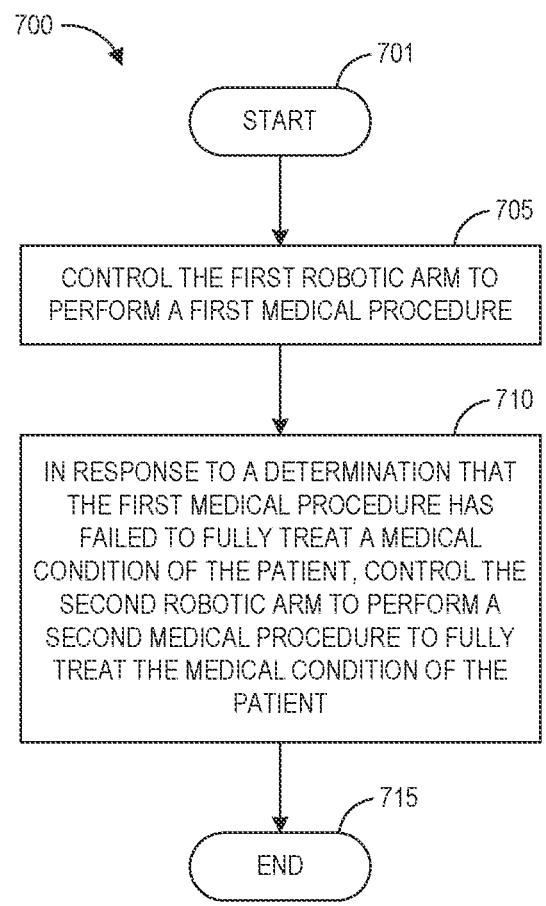
FIG. 28 is a flowchart illustrating an example method operable by a robotic system, or component(s) thereof, for performing concomitant medical procedures including procedure escalation in accordance with aspects of this disclosure.

FIG. 28 is a flowchart illustrating an example method operable by a robotic system, or component(s) thereof, for performing concomitant medical procedures including procedure escalation in accordance with aspects of this disclosure. For example, the steps of method 700 illustrated in FIG. 28 may be performed by one or more processor(s) and/or other component(s) of a medical robotic system (e.g., robotically enabled system 10, or one of the robotic medical systems 200, 300, or 400) or associated system(s). For convenience, the method 700 is described as performed by the "system" in connection with the description of the method 700.

The method 700 begins at block 701. The method 700 may be performed during the method 500 for performing concomitant medical procedures illustrated in FIG. 26, for example, between blocks 505 and 510. However, the timing of performing the method 700 is not limited, and may be performed before block 505, after block 510, or concurrently with one or more of blocks 505 and 510. At block 705, the system may control the first robotic arm to perform a first medical procedure. The first medical procedure may involve localizing the target site. The system may further select a site for an incision based on the localization of the target site. The incision may be used for delivering the second medical instrument used in the second medical procedure of block 710.

At block 710, in response to a determination that the first medical procedure has failed to fully treat a medical condition of the patient, the system may control the second medical procedure to perform a second medical procedure to fully treat the medical condition of the patient. The second medical procedure may have a higher level of invasiveness than the first medical procedure. The first medical procedure and the second medical procedure are performed concomitantly during a single medical episode. In some embodiments, the first medical procedure and the relatively more invasive second medical procedure are performed using a single platform, such as a cart-based platform or a bed-based platform with multiple arms. In other embodiments, the first medical procedure and the relatively more invasive second medical procedure are performed using multiple integrated platforms, such as a bed-based platform in combination with a cart-based platform or a cart-based platform in combination with another cart-based platform. In some embodiments, the system may further control the second robotic arm to perform the second medical procedure in response to a determination that a target site within an anatomy of the patient satisfies a condition for treatment via the second medical procedure. The method 700 ends at block 715.

C. User Interface for the Control of Multiple Medical Instruments.

Another aspect of this disclosure relates to a user interface which can enable a single user to control all of the robotic arms during a concomitant procedure. In other words, aspects of this disclosure relate to the use of a novel single interface which can be used to perform an endoscopic intervention using one or more flexible devices, as well as a laparoscopic intervention using one or more rigid devices.

Figure 29:
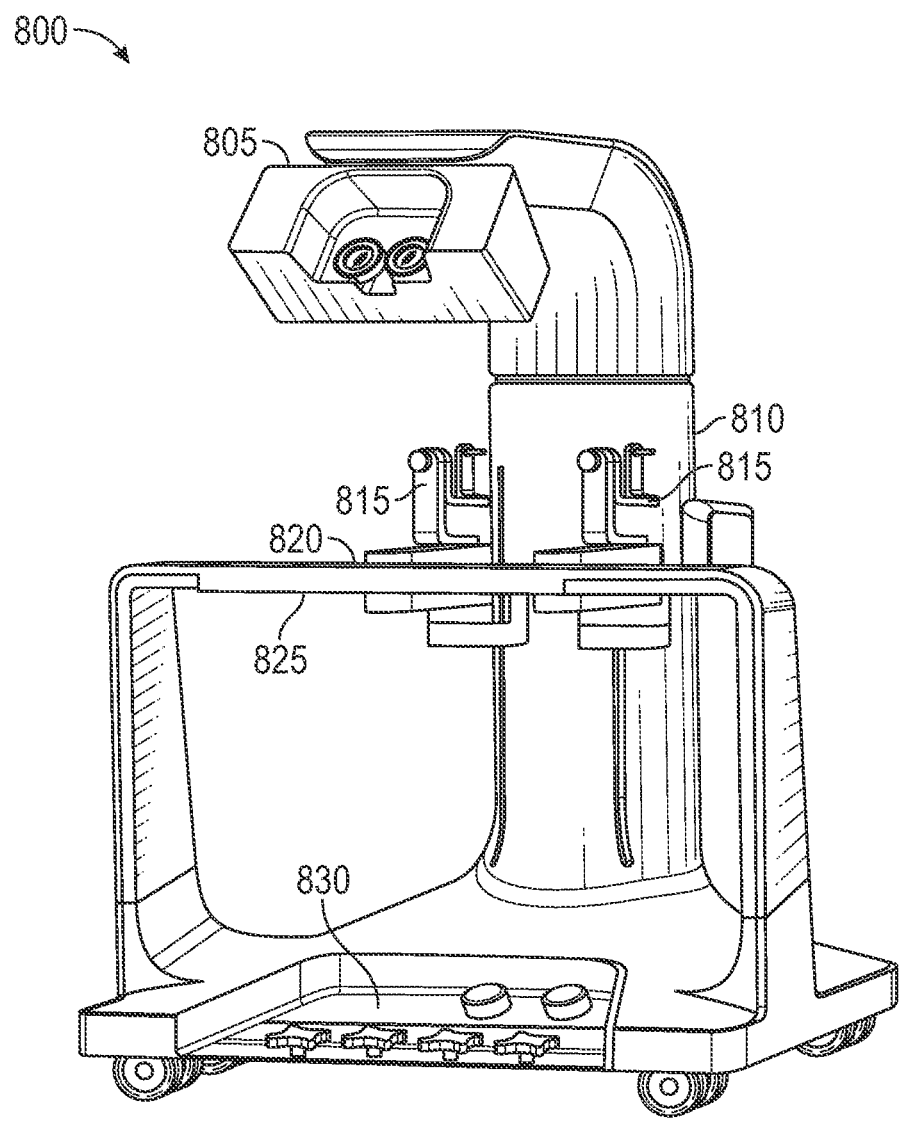
FIG. 29 illustrates an example console including one or more types of interfaces for controlling robotic arms in accordance with aspects of this disclosure.

FIG. 29 illustrates an example console including one or more types of interfaces for controlling robotic arms in accordance with aspects of this disclosure. As shown in FIG. 29, the console 800 includes a viewer 805, a controller 810 including two handles (also referred to as positioning platforms) 815, configured to received input from a user's left and right hands, a pendant 820, an armrest 825, and one or more foot pedals 830.

Figure 30:
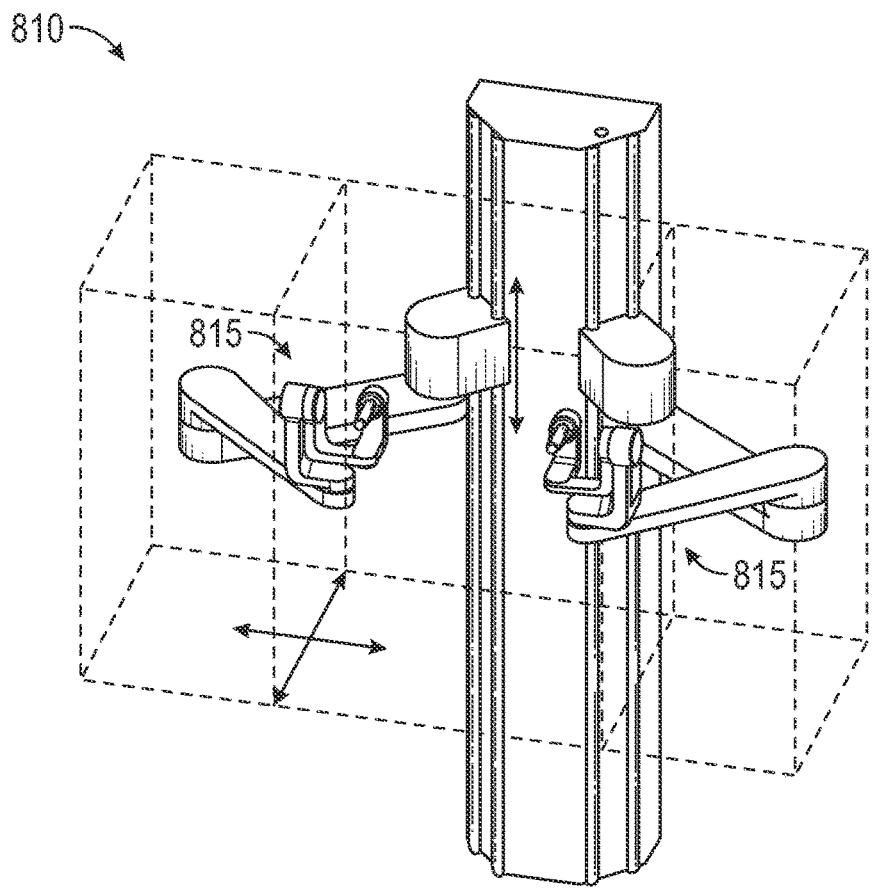
FIG. 30 illustrates a close-up view of the controller illustrated in FIG. 29 in accordance with aspects of this disclosure.
Figure 31:
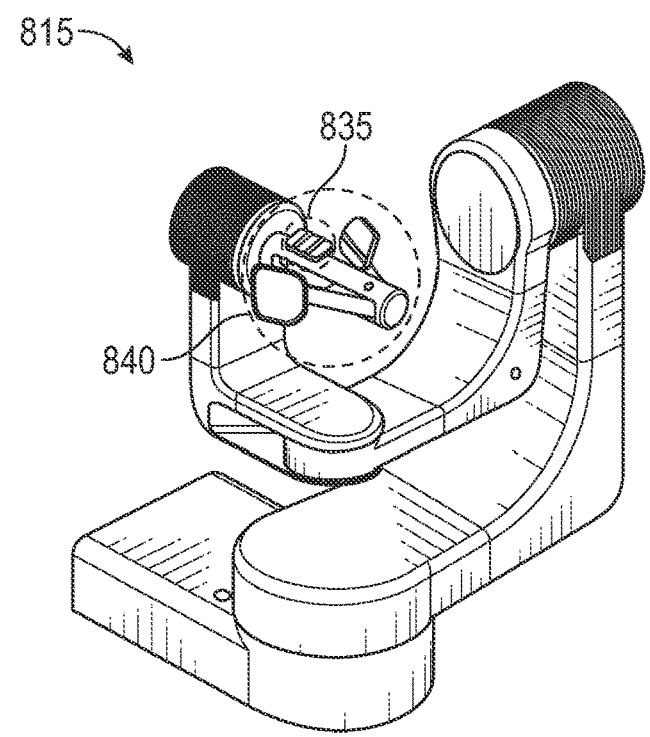
FIG. 31 illustrates a close-up view one of the handles illustrated in FIGS. 29 and 30 in accordance with aspects of this disclosure.

FIG. 30 illustrates a close-up view of the controller illustrated in FIG. 29 in accordance with aspects of this disclosure. The controller 810 of FIG. 30 may be similar to the controller 182 illustrated in FIG. 19. FIG. 31 illustrates a close-up view of one of the handles illustrated in FIGS. 29 and 30 in accordance with aspects of this disclosure. In some embodiments, the handle 815 includes a button 835 and finger-grips 840. The button 835 provides a user interface which allows the user to actuate an end effector of the corresponding medical instrument. The finger-grips 840 may provide an interface which allows the user to grab the handle 815 and manipulate the position of the handle 815 in six degrees of freedom. The handle 815 may also function as a gimbal allowing the user to manipulate the handle in the three orientation degrees of freedom (e.g., pitch, yaw, and roll).

Figure 32:
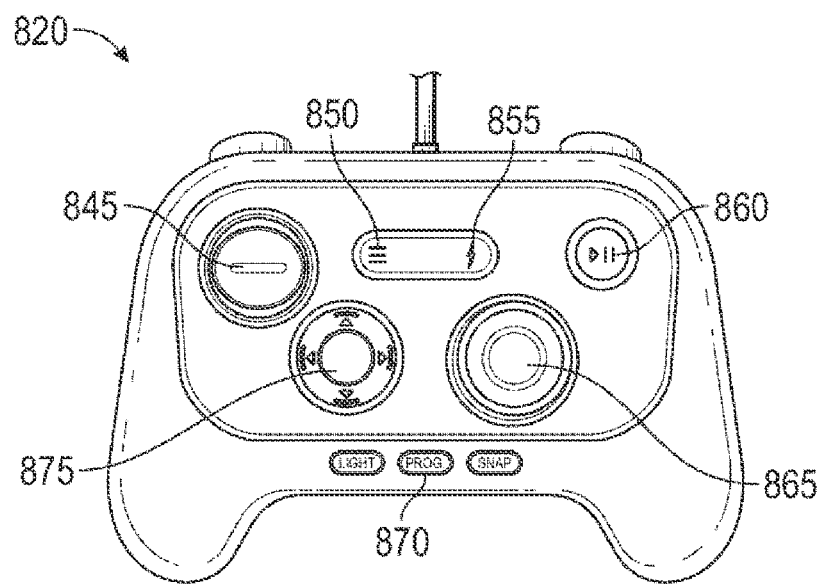
FIG. 32 illustrates a close-up view of the pendant illustrated in FIG. 29 in accordance with aspects of this disclosure.

FIG. 32 illustrates a close-up view of the pendant illustrated in FIG. 29 in accordance with aspects of this disclosure. The pendant 820 includes an insert/retract joystick 845, a menu button 850, a quick action button 855, a pause button 860, an articulate and relax joystick 865, snapshot, light, and one-programmable buttons 870, and a five button cluster button 875. The pendant 820 may be configured to drive a flexible instrument, such as the flexible instruments 230 of FIG. 21.

Although FIGS. 29-32 include two or more types of user interfaces (e.g., a gimbal-based interface and a pendant-based interface), in some embodiments, the console 800 may include a single type of interface, such as the handles 815 to perform the concomitant procedures disclosed herein. For example, in some embodiments, the left-hand handle 815 can be configured to control an endoscopic instrument while the right-hand handle 815 can be configured to control a laparoscopic instrument. In other embodiments, the left- and right-hand handles 815 can be used in two different modes—a first mode configured to control one or more flexible endoscopic instruments and a second mode configured to control one or more rigid laparoscopic instruments. The foot pedal 830 or other button on the console 800 may be configured to receive an input from the user to switch between the two modes. The use of a single type of interface to control two different instruments (e.g., a flexible endoscope and a rigid laparoscope) is highly novel, as a physician would often use two different types of interfaces to control such varied instrumentation.

While a controller 810 such as the controller 810 of FIG. 30 having left and right hand handles 815 may be used for controlling laparoscopic instruments, it may not be typical to use this type of controller 810 with concomitant endoscopic procedures involving one or more flexible devices. However, it may be desirable to provide a single user interface to the user to control two or more medical instruments (including an endoscopic instrument and laparoscopic instrument) through the same interface, so that the user does not have to continually switch between different user input device when switching between control of the two medical instruments. Thus, in order to provide a single interface through which the physical can control both, the controller 810 may be adapted to control an endoscopic instrument in addition to the laparoscopic instrument.

Figure 33:
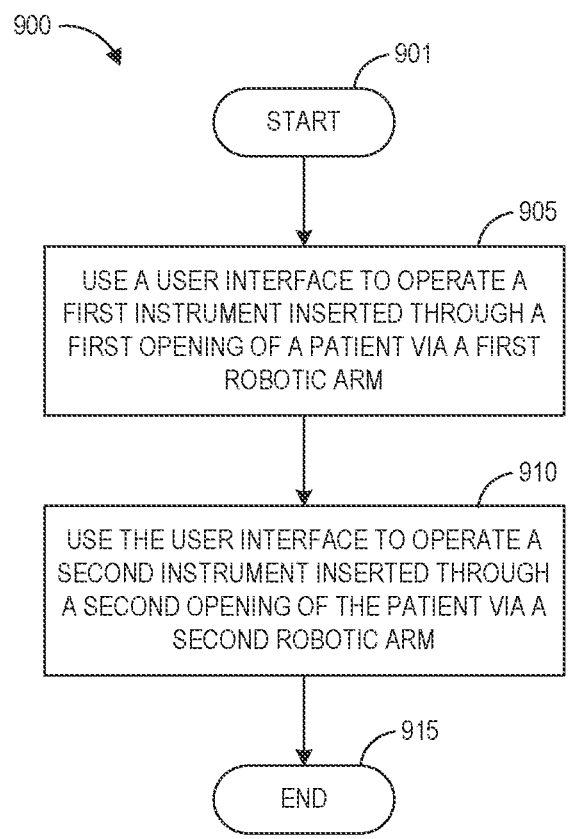
FIG. 33 is a flowchart illustrating an example method operable by a robotic system, or component(s) thereof, for performing concomitant medical procedures via a single user interface in accordance with aspects of this disclosure.

FIG. 33 is a flowchart illustrating an example method operable by a robotic system, or component(s) thereof, for performing concomitant medical procedures via a single user interface in accordance with aspects of this disclosure. For example, the steps of method 900 illustrated in FIG. 33 may be performed by processor(s) and/or other component(s) of a medical robotic system (e.g., robotically enabled system 10, or one of the robotic medical systems 200, 300, or 400) or associated system(s). For convenience, the method 900 is described as performed by the "system" in connection with the description of the method 900.

The method 900 begins at block 901. At block 905, the system may use a user interface to operate a first instrument inserted through a first opening of a patient via a first robotic arm. At block 910, the system may use the user interface to operate a second instrument inserted through a second opening of the patient via a second robotic arm. The first opening and the second opening are positioned at two different anatomical regions of the patient. In some embodiments, the first opening may be a natural orifice of the patient and the second opening may be an incision formed in the patient. The first instrument may be flexible, while the second instrument may be rigid. The method 900 ends at block 915.

In one embodiment, in response to the system received a selection from a user for control of endoscopic instruments, one of the handles 815 is mapped to control of insertion and retraction of the endoscopic instruments, while the other handle 815 is mapped to control of the articulation and roll of the endoscopic instrument. The handle 815 controlling insertion and retraction may be haptically constrained to move in a line and the controller 810 may include a clutch configured to allow the user to adjust the stroke length available to translate the endoscopic instrument into or out of the patient's body. The handle 815 controlling articulation and roll can be haptically constrained so that the handle 815 does not move in a planar fashion. The position of the other articulation/roll handle 815 can be fixed in a coordinate plane but allowed to rotate, pitch, and yaw. Accessory buttons 835 on the articulation/roll handle 815 can be configured to allow the user to irrigate or aspirate a lumen, as well as to deliver energy to the endoscopic instrument.

In a second embodiment, one of the handles 815 can be mapped to control of insertion and retraction of the endoscopic instruments, while the other handle 815 is mapped to control of the articulation and roll of the endoscopic instrument as in the first embodiment, but the driving experience for the user may be modified slightly. One handle 815 may be haptically constrained to move in a line, but rather than requiring the user to clutch, the user controller 810 may be configured such that the user simply moves his or her hand away or toward the procedural target thus translating the endoscopic instrument away from or toward a point of interest. The magnitude with which the user moves his or her hand can be mapped to the velocity with which the endoscopic instrument translates into or out of the patient's body. The remaining handle 815 may be configured to be controlled in similar fashion as described in the first embodiment.

A third embodiment may include the controller 810 having a secondary set of interfaces (not illustrated) in addition to the primary handles 815 illustrated in FIGS. 29-31. The primary left and right handles 815 can be configured similar to laparoscopic or thoracoscopic control interfaces. The secondary set of left and right interfaces can be configured to drive endoscopic instruments. One of the secondary interfaces can include a loop of endoscope-like insertion tube mounted on two wheels. The loop of insertion tube can be configured to be translated along an axis and rolled left and right. The insertion tube can provide either positional or velocity-based controls. There may be a toggle button on the controller 810 to allow the user to cycle through concentric instruments that need to be translated or rolled in the patient's body. Another secondary interface can include a mock endoscope tip that is enhanced with a series of buttons. The mock endoscope tip can be configured to be manipulated by the user to command the desired shape of the distal end of the robotic controlled endoscopic instrument. Buttons on the mock endoscope tip can be utilized to irrigate or aspirate within a lumen, as well as deliver energy to the endoscopic instrument. The mock endoscope tip may either assume the current position of endoscopic instrument being controlled and maintain that position until commanded otherwise by the user, or behave more like a traditional endoscopic instrument and only maintain a position when actively commanded by the user. Another secondary interface can include a "joy-stick" type button on one or more of the handles 815, which can be used to control one or more flexible instruments in a similar fashion to the inputs on pendant 820. In some embodiments, the handles 815 reposition themselves into an alternative configuration (e.g., such as pointing upwards) to facilitate ergonomic control of the secondary interface joystick buttons.

In a fourth embodiment, the controller 810 may include secondary interfaces to translate and roll the endoscopic instrument as described in the third embodiment, but one of two primary left or right hand interfaces can be configured to control endoscopic instrument articulation and other functions.

In a fifth embodiment, the controller 810 can include secondary interfaces which include a pendant 820 as shown in FIG. 32. In this embodiment, the user must physically switch back and forth between the left and right handle 815 surgical controls, and the pendant 820 to move between control of laparoscopic and endoscopic instruments. The current view displayed by the viewer 805 can be controlled by the controller 810.

In some embodiments, the console 800 is configured to restrict the number of robotic arms controllable by the simultaneously while constraining the motion of the other robotic arms. For example, in some embodiments, the interfaces can be used to drive a selected robotic arm, while constraining the motion of the other robotic arms (e.g., two, three, four or more).

D. Viewing and Switching Image Displays.

With reference to FIGS. 29-32, in some embodiments, the viewer 805 can be configured to display images from endoscopic and laparoscopic imaging sensors, as well as any preoperative plans or scans that have been loaded onto the system or other sources of live video such as an ultrasound probe. The user can toggle between the different views in various ways, including but not limited to: using the accessory button 835 located on left or right hand interfaces; using the accessory foot pedal 830 or a switch activated by the user's feet, knees, toes or elbow; using haptic enabled commands in combination with instrument clutching to toggle or cycle between multiple views using hand-based gestures via left and right hand interfaces; using the control pendant 825 attached to the console; or any combination. Secondary views may be displayed via picture-in-picture, side-by-side, split frame, or cyclical viewing modes.

Figure 34:
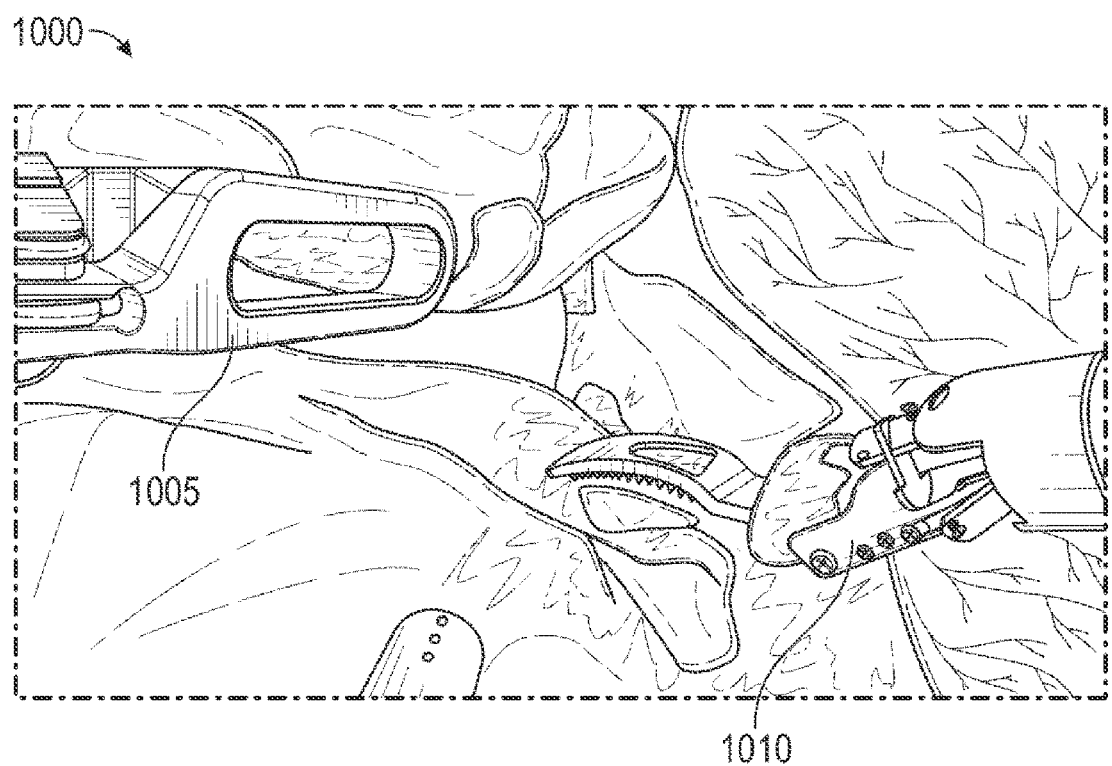
FIGS. 34 and 35 are example views which may be displayed by a viewer during concomitant medical procedures in accordance with aspects of this disclosure.
Figure 35:
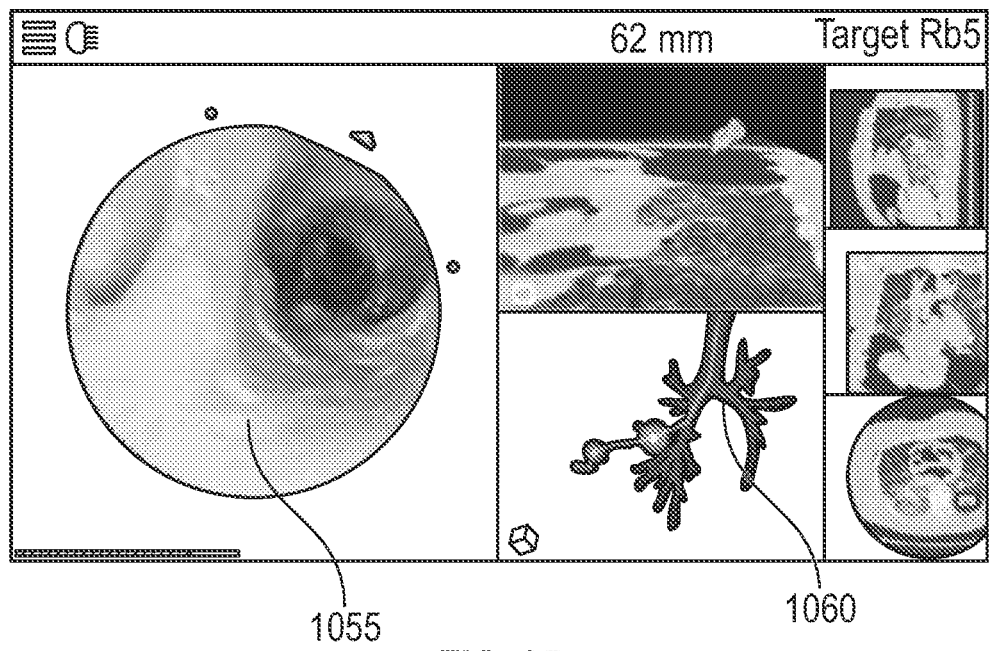

FIGS. 34 and 35 are example views which may be displayed by a viewer during concomitant medical procedures in accordance with aspects of this disclosure. In particular, FIG. 34 illustrates a thoracoscopic view 1000 while FIG. 35 illustrates an endoscopic view 1050.

In some embodiments, the control of the currently selected medical instrument is synchronized with the coordinate frame of the primary view displayed by the viewer 805. The system may consider the instruments originating from the approach of the primary view displayed as the primary instruments, however, the system may allow the user to control any instrument on the system relative to the primary view. In other words, in the scenario where the user is in the thoracoscopic viewing mode 1000, the thoracoscopic instruments are the primary instruments. As shown in the thoracoscopic viewing mode 1000 of FIG. 34, a first thoracoscopic instrument 1005 and a second thoracoscopic instrument 1010 can be seen.

The user may want to adjust the endoscope that is positioned within the lung. To do so, the user may display the appropriate secondary view (in this case endoscopic view 1050), and utilize one of the interfaces described above in "Section C." to toggle from a primary left or right hand instrument to a secondary left or right hand instrument, and adjust endoscopic instruments as necessary. As shown in FIG. 35, the endoscopic view 1050 may include a first view 1055 of an imaging device (e.g., a camera) on the endoscope and a second view 1060 illustrating the position of the tip of the endoscope with respect to a preoperative model. In addition to toggling between the thoracoscopic view 1000 and the endoscopic view 1050, the system may further be able to toggle between the thoracoscopic view 1000, the endoscopic view 1050, and a third view obtained via a pre-operative scan of the patient (e.g., in response to a user input via one of the user interfaces).

Figure 36:
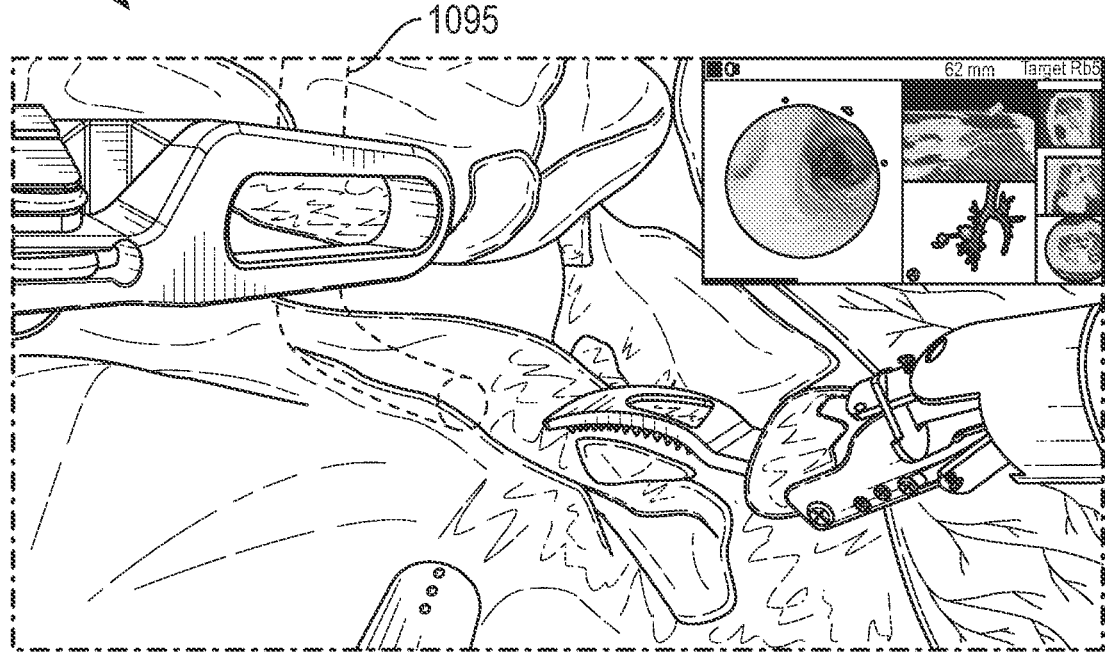
FIG. 36 is another example view which may be displayed by a viewer during concomitant medical procedures in accordance with aspects of this disclosure.

FIG. 36 is another example view which may be displayed by a viewer during concomitant medical procedures in accordance with aspects of this disclosure. In some embodiments, the system may be configured to have a computer-generated overlay of one image on top of another, as shown in FIG. 36. In fact, in the embodiment illustrated in FIG. 36, two separate view-on-view embodiments are illustrated. First, an endoscopic view (upper right hand corner) from a flexible scope is overlaid on the laparoscopic view 1090 from a rigid scope (base image). Second, a graphical or virtual representation 1095 of the flexible scope (in contour) is also overlaid on the laparoscopic view 1090 from the rigid scope. By providing such view-in-view capabilities, this helps a physician to perform multiple procedures concomitantly, and minimizes the need for unnecessary personnel to perform the individual procedures.

Figure 37:
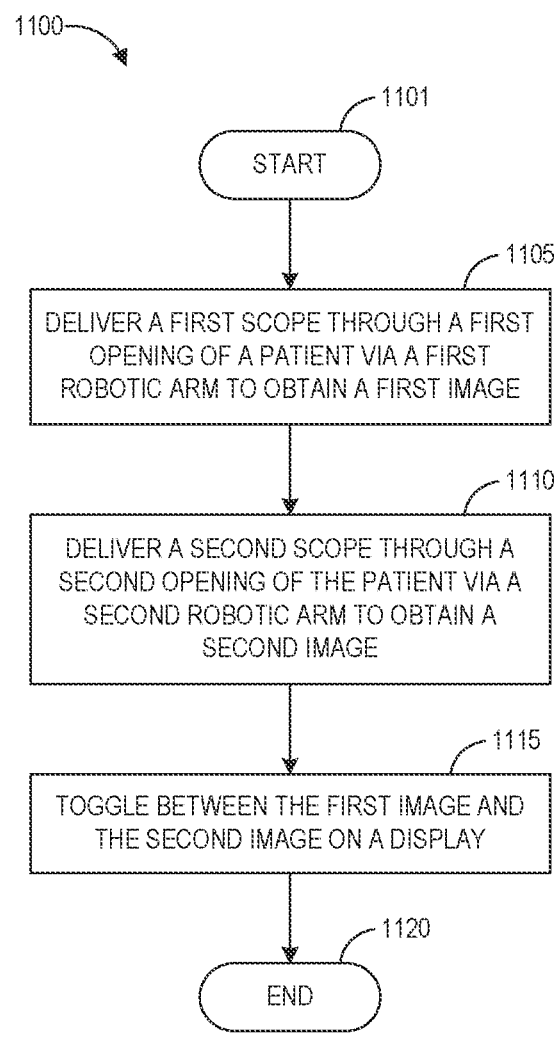
FIG. 37 is a flowchart illustrating an example method operable by a robotic system, or component(s) thereof, for toggling between displayed images while performing concomitant medical procedures in accordance with aspects of this disclosure.

FIG. 37 is a flowchart illustrating an example method operable by a robotic system, or component(s) thereof, for toggling between displayed images while performing concomitant medical procedures in accordance with aspects of this disclosure. For example, the steps of method 1100 illustrated in FIG. 37 may be performed by processor(s) and/or other component(s) of a medical robotic system (e.g., robotically enabled system 10, or one of the robotic medical systems 200, 300, or 400) or associated system(s). For convenience, the method 1100 is described as performed by the "system" in connection with the description of the method 1100.

The method 1100 begins at block 1101. At block 1105, the system may deliver a first scope through a first opening of a patient via a first robotic arm to obtain a first image. At block 1110, the system may deliver a second scope through a second opening of the patient via a second robotic arm to obtain a second image. At block 1115, the system may toggle between the first image and the second image on a display. In some embodiments, the system may further be configured to toggle to a view in which the first image is overlaid on the second image on the display. In other embodiments, the system may be configured to toggle between toggling between the first image, the second image, and a third image obtained from a pre-operative scan of the patient (e.g., a computed tomography (CT) scan or a fluoroscopic scan). The system may further be configured to overlay a virtual image over either (or at least one of) the first image or the second image on the display, as shown in FIG. 36. The method 1100 ends at block 1120.

3. Implementing Systems and Terminology

Implementations disclosed herein provide systems, methods and apparatus for performing concomitant medical procedures.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions associated with the systems and methods for performing concomitant medical procedures described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical method, comprising:
   electronically controlling a first robotic arm and a second robotic arm to insert a first medical instrument through a first opening of a patient, the first medical instrument comprising a flexible instrument;
   electronically controlling a third robotic arm to insert a second medical instrument through a second opening of the patient, wherein the first opening and the second opening are positioned at two different anatomical regions of the patient;
   controlling the first robotic arm to treat a medical condition of the patient by performing a first medical procedure; and
   in response to a determination that the first medical procedure has failed to fully treat the medical condition, controlling the third robotic arm to treat the medical condition by performing a second medical procedure different from and more invasive than the first medical procedure.

2. The method of claim 1, wherein the first robotic arm and the second robotic arm are coupled to a first vertically movable robotic arm support.

3. The method of claim 2, further comprising electronically controlling the first vertically movable robotic arm support to robotically move in a vertical plane.

4. The method of claim 2, wherein the first vertically movable robotic arm support is attached to a table support structure of an operating table.

5. The method of claim 4, further comprising electronically controlling the first robotic arm to robotically move in a horizontal plane along the first vertically movable robotic arm support and relative to a longitudinal length of the operating table.

6. The method of claim 5, wherein electronically controlling the first robotic arm to robotically move in the horizontal plane along the first vertically movable robotic arm support and relative to the longitudinal length of the operating table causes the first robotic arm to move in the horizontal plane along the first vertically movable robotic arm support and relative to the second robotic arm.

7. The method of claim 1, wherein:
   the first robotic arm is coupled to a first vertically movable robotic arm support; and
   the second robotic arm is coupled to a second vertically movable robotic arm support.

8. The method of claim 7, further comprising:
   electronically controlling the first vertically movable robotic arm support to robotically move in a first vertical plane; and
   electronically controlling the second vertically movable robotic arm support to robotically move in a second vertical plane.

9. The method of claim 8, wherein the first vertically movable robotic arm support and the second vertically movable robotic arm support are attached to a table support structure of an operating table.

10. The method of claim 8, further comprising positioning the second vertically movable robotic arm support at a height that is different from the first vertically movable robotic arm support.

11. The method of claim 9, further comprising electronically controlling the first robotic arm to robotically move in a horizontal plane along the first vertically movable robotic arm support and relative to a longitudinal length of the operating table.

12. The method of claim 11, wherein electronically controlling the first robotic arm to robotically move in the horizontal plane along the first vertically movable robotic arm support and relative to the longitudinal length of the operating table causes the first robotic arm to move in the horizontal plane along the first vertically movable robotic arm support and relative to the second robotic arm.

13. The method of claim 9, further comprising electronically controlling the second robotic arm to robotically move in a horizontal plane along the second vertically movable robotic arm support and relative to a longitudinal length of the operating table.

14. The method of claim 13, wherein electronically controlling the second robotic arm to robotically move in the horizontal plane along the second vertically movable robotic arm support and relative to the longitudinal length of the operating table causes the second robotic arm to move in the horizontal plane along the second vertically movable robotic arm support and relative to the first robotic arm.

15. The method of claim 1, wherein the first opening is a natural orifice of the patient and the second opening is an incision formed in the patient.

16. The method of claim 1, wherein the second medical instrument comprises a rigid instrument.

17. The method of claim 1, further comprising:
   receiving instructions to control movement of the first robotic arm via a pendant; and receiving instructions to control movement of the second robotic arm via a gimbal attached to a positioning platform.

18. The method of claim 1, wherein the first medical procedure and the second medical procedure are performed concomitantly during a single medical episode.

19. A system, comprising:
- a set of robotic arms comprising a first robotic arm, a second robotic arm, and a third robotic arm;
- at least one computer-readable memory having stored thereon executable instructions; and
- one or more processors in communication with the at least one computer-readable memory and configured to execute the instructions to cause the system to at least:
  - control the first robotic arm and the second robotic arm to insert a first medical instrument through a first opening of a patient, the first medical instrument comprising a flexible instrument;
  - control the third robotic arm to insert a second medical instrument through a second opening of the patient, wherein the first opening and the second opening are positioned at two different anatomical regions of the patient;
  - control the first robotic arm to treat a medical condition of the patient by performing a first medical procedure; and
  - in response to a determination that the first medical procedure has failed to fully treat the medical condition, control the third robotic arm to treat the medical condition by performing a second medical procedure different from and more invasive than the first medical procedure.

* * * * *